United States Patent
Saraliev et al.

(10) Patent No.: US 10,639,805 B2
(45) Date of Patent: May 5, 2020

(54) MECHANICAL WRIST JOINTS WITH ENHANCED RANGE OF MOTION, AND RELATED DEVICES AND METHODS

(71) Applicant: INTUITIVE SURGICAL OPERATIONS, INC., Sunnyvale, CA (US)

(72) Inventors: Daniel P. Saraliev, Soquel, CA (US); Gabriel F. Brisson, Albany, CA (US); Matthew R. Williams, Walnut Creek, CA (US)

(73) Assignee: INTUITIVE SURGICAL OPERATIONS, INC, Sunnyvale, CA (US)

( * ) Notice: Subject to any disclaimer, the term of this patent is extended or adjusted under 35 U.S.C. 154(b) by 575 days.

(21) Appl. No.: 15/119,192

(22) PCT Filed: Feb. 20, 2015

(86) PCT No.: PCT/US2015/016879
§ 371 (c)(1),
(2) Date: Aug. 16, 2016

(87) PCT Pub. No.: WO2015/127250
PCT Pub. Date: Aug. 27, 2015

(65) Prior Publication Data
US 2017/0120457 A1    May 4, 2017

Related U.S. Application Data

(60) Provisional application No. 61/943,068, filed on Feb. 21, 2014.

(51) Int. Cl.
*A61B 34/30* (2016.01)
*B25J 17/02* (2006.01)
(Continued)

(52) U.S. Cl.
CPC ........... *B25J 17/0241* (2013.01); *A61B 34/30* (2016.02); *A61B 34/35* (2016.02); *A61B 34/37* (2016.02);
(Continued)

(58) Field of Classification Search
CPC ....... B25J 17/0241; B25J 9/104; A61B 34/30; A61B 34/35; A61B 34/37; A61B 34/71;
(Continued)

(56) References Cited

U.S. PATENT DOCUMENTS

| | | |
|---|---|---|
| 5,755,731 A | 5/1998 | Grinberg |
| 6,817,974 B2 | 11/2004 | Cooper et al. |

(Continued)

FOREIGN PATENT DOCUMENTS

| | | |
|---|---|---|
| CN | 102046101 A | 5/2011 |
| WO | WO-2009145572 A2 | 12/2009 |

(Continued)

OTHER PUBLICATIONS

International Search Report and Written Opinion for Application No. PCT/US2015/016879, dated Jun. 8, 2015, 16 pages.

(Continued)

*Primary Examiner* — Michael W Kahelin
*Assistant Examiner* — Shirley X Jian
(74) *Attorney, Agent, or Firm* — Jones Robb, PLLC

(57) ABSTRACT

A wrist joint, such as for a surgical instrument, may include a first disc, a second disc adjacent the first disc, and a drive tendon that extends through the first disc and the second disc. The first disc and the second disc may include respective opposing joint features that intermesh with one another. The first disc and the second disc may further include opposing load bearing surfaces separate from the joint features. The drive tendon may exert a force on at least one of the first and second discs to cause relative rotation (Continued)

between the first and second discs. The first and second discs may have a maximum rotational range of motion greater than about +/−45 degrees relative to each other.

19 Claims, 20 Drawing Sheets

(51) Int. Cl.
*B25J 9/10* (2006.01)
*A61B 34/00* (2016.01)
*A61B 34/35* (2016.01)
*A61B 34/37* (2016.01)
*A61B 50/13* (2016.01)
*A61B 90/00* (2016.01)
*A61B 17/29* (2006.01)

(52) U.S. Cl.
CPC .............. *A61B 34/71* (2016.02); *A61B 50/13* (2016.02); *A61B 90/361* (2016.02); *B25J 9/104* (2013.01); *A61B 2017/2908* (2013.01); *A61B 2034/306* (2016.02); *Y10S 901/29* (2013.01)

(58) Field of Classification Search
CPC . A61B 90/361; A61B 50/13; A61B 2034/306; A61B 2017/2908; Y10S 901/29
See application file for complete search history.

(56) References Cited

U.S. PATENT DOCUMENTS

| | | |
|---|---|---|
| 7,682,307 B2 | 3/2010 | Danitz et al. |
| 8,887,595 B2 | 11/2014 | Williams et al. |
| 2010/0249759 A1 | 9/2010 | Hinman et al. |
| 2011/0152879 A1* | 6/2011 | Williams ............... A61B 34/30 606/130 |
| 2011/0196419 A1 | 8/2011 | Cooper |
| 2012/0220831 A1 | 8/2012 | Cooper et al. |
| 2015/0202013 A1 | 7/2015 | Teichtmann et al. |

FOREIGN PATENT DOCUMENTS

| | | |
|---|---|---|
| WO | WO-2011078971 A1 | 6/2011 |
| WO | WO-2013162206 A1 | 10/2013 |
| WO | WO-2014016337 A1 | 1/2014 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP15752516.3, dated Oct. 23, 2017, 9 pages.

* cited by examiner

MECHANICAL WRIST JOINTS WITH ENHANCED RANGE OF MOTION, AND RELATED DEVICES AND METHODS

CROSS-REFERENCE TO RELATED APPLICATIONS

This application is the U.S. national phase of international application no. PCT/US2015/016879 (filed Feb. 20, 2015), which designated the United States and claimed right of priority to U.S. provisional patent application No. 61/943,068 (filed Feb. 21, 2014), both of which are incorporated herein by reference.

TECHNICAL FIELD

Aspects of the present disclosure relate to articulatable wrist joints, and to surgical instruments and related systems and methods utilizing such wrist joints.

BACKGROUND

Remotely controlled surgical instruments (also referred to as teleoperated surgical instruments) are often used in minimally invasive medical procedures. A surgical instrument may include joints to position the surgical instrument in a desired location. Because the range of motion of an individual joint can be limited, multiple joints having the same or similar motion may be necessary to provide a desired range of motion that exceeds the range of motion for an individual joint. However, use of multiple joints requires additional components to control and support the additional joints, which can increase the complexity in operation, overall size, and difficulty of manufacturing the instrument.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a wrist joint comprises a first disc, a second disc adjacent the first disc, and a drive tendon that extends through the first disc and the second disc. The first disc and the second disc may comprise respective opposing joint features that intermesh with one another. The first disc and the second disc may further comprise opposing load bearing surfaces separate from the joint features. The drive tendon may be configured to exert a force on at least one of the first and second discs to cause relative rotation between the first and second discs. The first and second discs may have a maximum rotational range of motion greater than about +/−45 degrees relative to each other.

In accordance with at least one exemplary embodiment, a surgical instrument comprises a shaft, an end effector coupled to a first end of the shaft, a transmission mechanism, and a wrist joint. The transmission mechanism may be disposed at a second end of the shaft opposite the first end. The transmission mechanism may transmit drive forces through actuation elements to actuate the end effector. The wrist joint may couple the end effector to the shaft. The wrist joint may comprise a pair of adjacent discs coupled together and have a maximum range of motion greater than +/−45 degrees.

In accordance with at least one exemplary embodiment, a surgical instrument comprises a shaft, an end effector coupled to a first end of the shaft, a transmission mechanism, and an articulatable wrist. The transmission mechanism may be disposed at a second end of the shaft opposite the first end. The transmission mechanism may transmit drive forces through actuation elements to actuate the end effector. The articulatable wrist may couple the end effector to the shaft. The articulatable wrist may comprise a first disc and a second disc. The first disc may have a plurality of teeth and a first load bearing surface separate from the plurality of teeth. The second disc may have a plurality of pins configured to intermesh with the teeth and a second load bearing surface separate from the plurality of pins. Further, the first load bearing surface and the second load bearing surface may engage each other to bear compressive forces of the wrist.

In accordance with at least one exemplary embodiment, a method of articulating a wrist joint comprises applying a force to a drive tendon coupled to at least one of a first disc and a second disc of the wrist joint, causing the first disc and the second disc to rotate relative to one another. During rotation of the first and second discs, at least one of a plurality of teeth of one of the first and second discs remain intermeshed with at least one of a plurality of pins of the other of the first and second discs when the discs are rotated relative to one another more than about +/−45 degrees, and load bearing surfaces of the first and second discs remain in contact with one another. Further, the load bearing surfaces of the first and second discs are radially spaced from the teeth and pins.

In accordance with at least one exemplary embodiment, a method of making a wrist joint comprises configuring a first disc with a plurality of teeth and a first load bearing surface separate from the plurality of teeth. The method may further comprise configuring a second disc with a plurality of pins and a second load bearing surface separate from the plurality of pins. A drive tendon may be extended through the first disc and the second disc. The method may further comprise coupling the first and second disc to one another so that the first and second joint features intermesh and the first and second load bearing surfaces contact one another. Further, the first and second discs may have a maximum rotational range of motion greater than about +/−45 degrees relative to each other.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present disclosure and together with the description serve to explain certain principles and operation.

DETAILED DESCRIPTION

Figure 1:
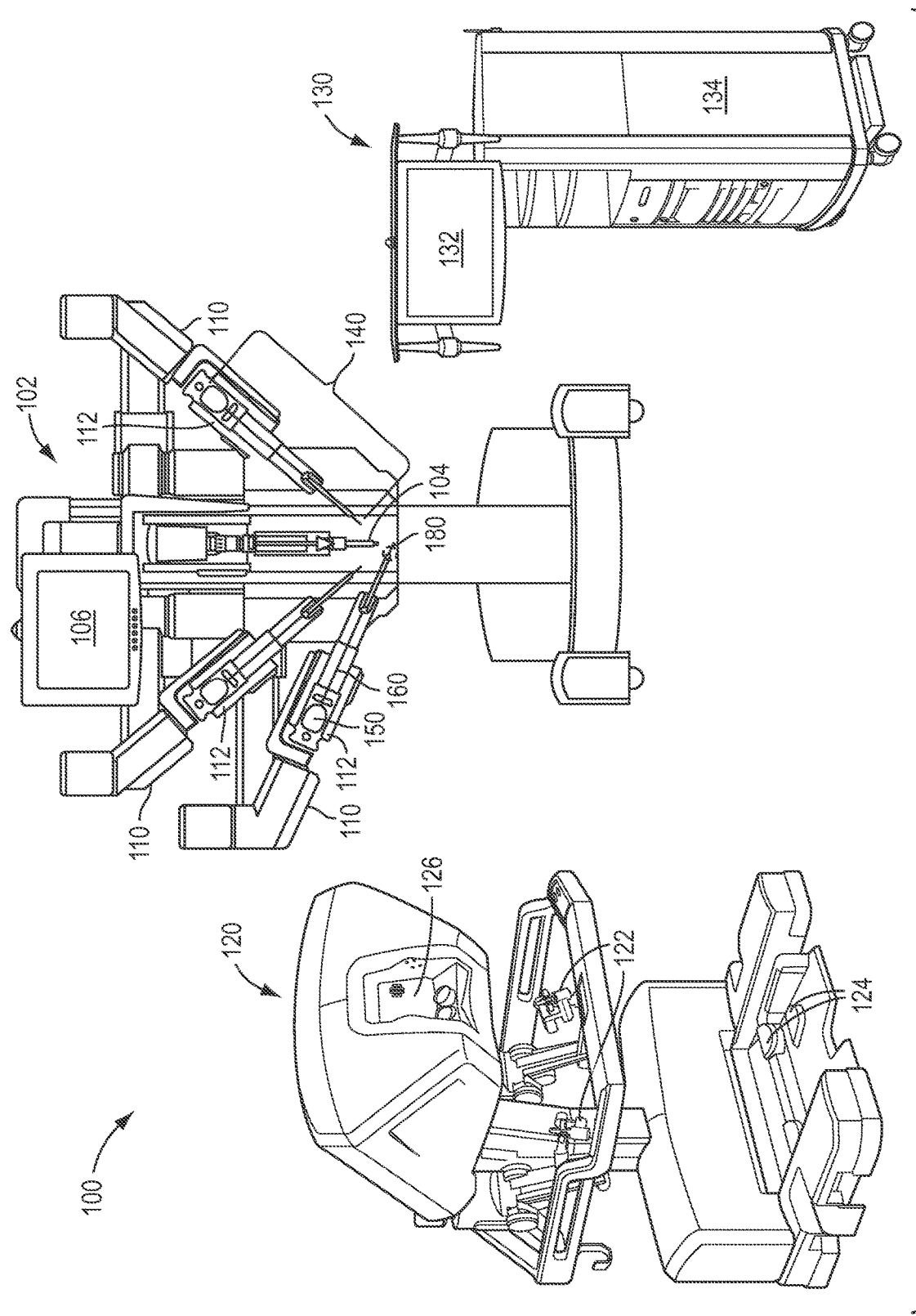
FIG. 1 shows a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", "clockwise", "counterclockwise", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates surgical instruments that include a joint that can achieve a relatively large range of motion. For example, a joint may have a maximum range of motion that permits discs of the joint to rotate relative to each other more than +/−45 degrees. In one example, a joint may include a plurality of teeth and pins that intermesh with one another so the joint may have repeatable movements. A disc may include one or more recesses to accommodate a tooth of another disc. A recess, for example, may have a trochoid shape. In another example, a joint may have a plurality of teeth to engage with pins and a separate load bearing surface. The load bearing surface may be located radially inward, such as a location closer to a central aperture of a disc than the teeth or pins of the disc, or the load bearing surface may be located radially outward, such as a location further from a central aperture of a disc than the teeth or pins of the disc. The load bearing surface may have a shape of a partial cylinder, a cycloidal shape, the shape of pins, or other shapes. In another example, the positions of pins of a disc may be altered relative to a circular arc, which may represent a contact surface between discs, such as a load bearing surface, and a theoretical arc through points of contact between pins and gears. For a disc having a load bearing surface with a partial cylindrical shape, the circular arc may have the same shape as the surface of the load bearing surface. By altering the position of one or more pins relative to the arc, the ease of manufacturing the disc and the smoothness of the disc's motion may be affected. For instance, all pins of the disc may be located on the circular arc, all pins may be offset from the circular arc, or at least one pin may be offset and at least one pin may be located on the circular arc. There may also be multiple pins, with the pins offset a different distance from the circular arc from one another.

Turning to FIG. 1, an example of a teleoperated surgical system 100 is shown that can employ surgical instruments in accordance with embodiments described herein. System 100, which may, for example, be a da Vinci® Surgical System available from Intuitive Surgical, Inc., includes a patient side cart 102 having multiple surgical instruments 140, each of which is mounted in a docking port on a robotic arm 110. Instruments 140 can be interchangeable, so that the instruments 140 mounted on arms 110 can be selected for a particular medical procedure or changed during a medical procedure to provide the clinical functions needed. As is well known in the art, surgical instruments 140 can implement many functions including, but not limited to, for example, forceps or graspers, needle drivers, scalpels, scissors, cauterizing tools, and staplers.

Figure 2:
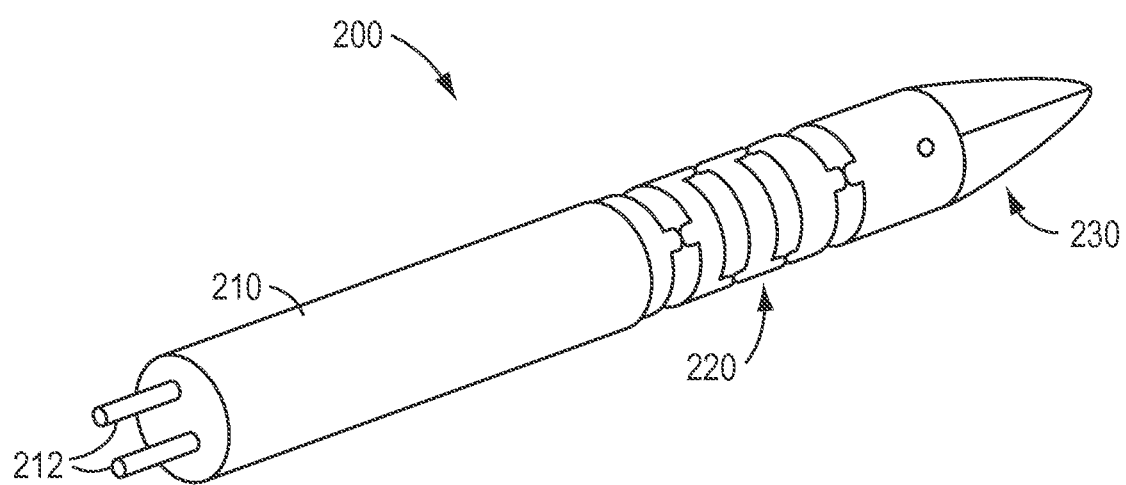
FIG. 2 shows a portion of distal end of a surgical instrument, according to an exemplary embodiment.

Each instrument 140 generally includes a transmission or backend mechanism 150, a main shaft 160 extending from the transmission mechanism 150, an optional wrist mechanism (not shown in FIG. 1) at the distal end of main shaft 160, and an end effector 180 extending from wrist mechanism or directly from the shaft 160. FIG. 2 illustrates a distal end 200 of a surgical instrument that includes a shaft 210, a wrist 220 at a distal end of shaft 210, and an end effector 230 extending from wrist 220.

Actuation elements 212, such as, for example, pull/pull tendons or push/pull rods, and electrical conductors that are connected to a wrist mechanism 220 and/or end effector 230 of an instrument may extend through shaft 210 of instrument, as shown in FIG. 2. Further, the actuation elements may extend through main shaft 160 and connect to transmission mechanism 150. Transmission mechanism 150 typically provides a mechanical coupling of the drive tendons to drive motors in patient side cart 102. For instance, transmission mechanisms 150 may be configured to connect to patient side manipulators 112 of arms 110 of the patient side cart 102.

The actuation interface may generally include drive motors that provide mechanical power for operation of surgical instruments 140. System 100 can thus control movement and tension in the tendons as needed to move or position wrist mechanism and operate end effector 180. An arm 110 of patient side cart 102 can be used to insert the end of a surgical instrument 140 through a cannula in small incisions in a patient undergoing a medical procedure and to operate a wrist mechanism of instrument 140 and/or end effector 180 at a worksite inside the patient.

A camera instrument 104 can similarly be mounted on an arm of cart 102 and optionally also have a wrist mechanism that system 100 operates to position a distal end of camera system 104 for viewing of a work site and the operation of surgical instruments 140 within a patient. The views from camera system 104, which may be stereoscopic or three-dimensional, can be viewed at a control console (not shown) and images may be displayed on a monitor 106. A processing system of system 100 can thus provide a user interface enabling a doctor or other medical personnel to see and manipulate the camera system 104 and instruments 140. For example, as with surgical instruments 140, an arm 110 can be used to insert the end of a camera instrument 104 through a cannula in small incisions in a patient undergoing a medical procedure and to operate wrist mechanism and/or end effector 180 at a worksite inside the patient.

The diameter or diameters of main shaft 160, wrist mechanism, and end effector 180 for surgical instrument 140 and the diameter of camera instrument 104 are generally selected according to the size of the cannula with which the instrument will be used. In an exemplary embodiment, a diameter of camera instrument 104 and a diameter of wrist mechanism and main shaft 160 may range from about 3 mm to about 13 mm. For example, the diameter may be about 4 mm, about 5 mm, or about 8 mm to match the sizes of some existing cannula systems.

As illustrated in the schematic view of FIG. 1, the teleoperated surgical system 100 may further include a surgeon console 120 and an auxiliary control/vision cart 130. In general, the surgeon console 120 receives inputs from a user, e.g., a surgeon, by various input devices, including but not limited to, gripping mechanisms 122 and foot pedals 124, and serves as a master controller to which the instruments 140 mounted at the patient side cart 102 are responsive to implement the desired motions of the surgical instrument(s) 102, and accordingly perform the desired surgical procedure. For example, while not being limited thereto, the gripping mechanisms 122 may act as "master" devices that may control the surgical instruments 140 and/or camera instrument 104, which may act as the corresponding "slave" devices at the robotic arms 110. For instance, gripping mechanisms 122 may control an end effector 180 and/or wrist of the surgical instrument 140, as those having ordinary skill in the art are familiar with. Further, while not being limited thereto, the foot pedals 124 may be depressed to provide, for example, monopolar or bipolar electrosurgical energy, or to activate a variety of other functions (e.g., suction, irrigation, and/or various other flux delivery modes) of the instruments 140. In other words, based on the commands provided to input devices at, for example, the surgeon console 120, the patient side cart 102 can position and actuate the instruments 140, 104 to perform a desired medical procedure via the patient side manipulators 112 at the arms 110. Thus, the instruments 140, 104 of patient side cart 102 may be remotely teleoperated according to commands input by a user at the surgeon console 120. Surgeon console 120 may further include a display to allow a surgeon to view a three-dimensional image of the surgical site, for example, during the surgical procedure, e.g., via the camera instrument 104 at the patient side cart 102.

In non-limiting exemplary embodiments of the teleoperated surgical system, the control/vision cart 130 includes "core" processing equipment, such as core processor 134, and/or other auxiliary processing equipment, which may be incorporated into or physically supported at the control/vision cart 130. The control/vision cart 130 may also include other controls for operating the surgical system. In an exemplary embodiment, signal(s) or input(s) transmitted from surgeon console 120 may be transmitted to one or more processors at control/vision cart 130, which may interpret the input(s) and generate command(s) or output(s) to be transmitted to the patient side cart 102 to cause manipulation of one or more of surgical instruments 140 and/or arms 110 to which the surgical instruments 140 are coupled at the patient side cart 102. It is noted that the system components in FIG. 1 are not shown in any particular positioning and can be arranged as desired, with the patient side cart 102 being disposed relative to the patient so as to affect surgery on the patient.

Surgical instrument joints, such as wrist joints, may move according to one or more degrees of freedom to provide motion to a surgical instrument or a camera instrument that includes the joint. For instance, a joint may include a plurality of members that may move relative to one another in one or more degrees of freedom (e.g., arbitrarily defined as pitch and/or yaw). A joint of a surgical instrument or a camera instrument may include various numbers of members. For example, a joint of a surgical instrument or a camera instrument may be a one-piece joint (e.g., a single piece designed to bend in one or more directions, such as due to structurally flexible portions provided in the piece), a two-piece joint (such as two discs, which may also be referred to as vertebrae, directly connected to one another), a three-piece joint (such as two discs and a third piece connecting the two discs), or joints including greater numbers of pieces.

Although the description below discusses joint configurations in the context of their application in surgical instruments, a person of ordinary skill in the art would understand that the joint configurations may be applied to camera instruments. Further, although the description below discusses joint configurations that are two-piece joints, the concepts of the description may also apply to joints including larger numbers of pieces, such as a three-piece joint or a joint including a greater number of pieces.

Joint members of the exemplary embodiments described herein may include features having cycloidal surface profiles, for example as are described in U.S. Pub. No. US 2011/0152879 to Williams, which is hereby incorporated by reference herein in its entirety. Joint members having cycloidal shapes are less prone to jamming, such as when joint members are compressed together, in comparison to joint members having more common involute shapes. In addition, the epicycloid 310 and the hypocycloid 320 shown in FIG. 3 of U.S. Pub. No. US 2011/0152879 include concave and convex contact areas, which provide relatively large contact areas for distributing forces between cycloids 310, 320. As a result, the stress between cycloidal surfaces may be reduced for a given load and cycloidal surfaces may experience reduced deformation under load.

As discussed in U.S. Pub. No. US 2011/0152879 to Williams, geared movement in a wrist mechanism may result when two members in the wrist mechanism have relative angular orientations that change according to a fixed relationship or gear ratio. As shown in FIGS. 1A and 1B of U.S. Pub. No. US 2011/0152879, members 110, 120 of a wrist joint 100 may respectively have bearing surfaces 112, 122 that are circular, permitting surfaces 112, 122 to roll on each other during geared movement when members 110, 120 rotate relative to one another. Member 110 may include a tooth 114 that can engage the walls of an aperture (recess) 124 of member 120 to prevent slipping, such as due to translation movement between members 110, 120. The combination of tooth 114 and walls of aperture 124 may be referred to as a pin gear. Therefore, a joint may include features to minimize or eliminate translation of joint members relative to one another. A surgical instrument, such as a wrist of a surgical instrument, may include a plurality of joints that bend in this manner. For instance, a surgical instrument may include multiple joints oriented relative to one another to provide multiple degrees of freedom for motion of the surgical instrument, such as via bending in pitch and yaw directions.

According to an exemplary embodiment, features of joint members used to minimize or eliminate translation between joint members may also enhance the repeated movement of joint members. For instance, after members 110, 120 have been rotated relative to one another, as shown in FIGS. 1A and 1B of U.S. Pub. No. US 2011/0152879, such as to bend a wrist of a surgical instrument, a user may wish to straighten the wrist, such as by reversing the rotation of members 110, 120. If either rotation resulted in a substantial displacement of members 110, 120 relative to one another in a lateral direction and/or a direction along a longitudinal axis of a surgical instrument, subsequent movements of members 110, 120 relative to one another may be less smooth. Further, substantial displacement between members 110, 120 could affect the control of movement between the members 110, 120 and a user may observe the displacement. By respectively providing members 110, 120 with tooth 114 and aperture 124, repeated movement of members 110, 120 may be enabled with minimal translation. Thus, joint members may be configured to have substantially repeatable movements. This ability of joint members to repeat movements by substantially returning joint members to their original positions may be referred to as the timing of a joint. For example, tooth 114 of member 110 and aperture 124 of member 120 may act as structures to provide timing to substantially return members 110, 120 to their original positions, such as the neutral state shown in the exemplary embodiment of FIG. 1A of U.S. Pub. No. US 2011/0152879.

In pin gears of joint discs, such as the pin gear provided by tooth 114 of member 110 and aperture 124 of member 120 of U.S. Pub. No. US 2011/0152879, a maximum amount of rotation permitted between adjacent discs including a pin gear may be limited to, for example, about +/−45 degrees relative to a longitudinal axis of a joint. A maximum range of motion of, for example, up to about +/−90 degrees may be achieved for the overall motion of a wrist of a surgical instrument by using two sets of disc joints that include a pin gear, with each set of disc joints providing a maximum rotation of +/−45 degrees relative to a longitudinal axis of a joint. However, the use of two sets of disc joints imposes an additional manufacture cost and requires other additional parts, such as control cables and motors in the backend components, for a surgical instrument. In view of these considerations, it may be desirable to provide a wrist joint having a relatively large maximum range of motion, for example, greater than about +/−45 degrees. Thus, in such a wrist joint, the joint may provide a controlled, articulated motion through and greater than about +/−45 degrees. In addition, it may be desirable to provide a wrist with a smooth motion and achieves "timing."

Figure 3:
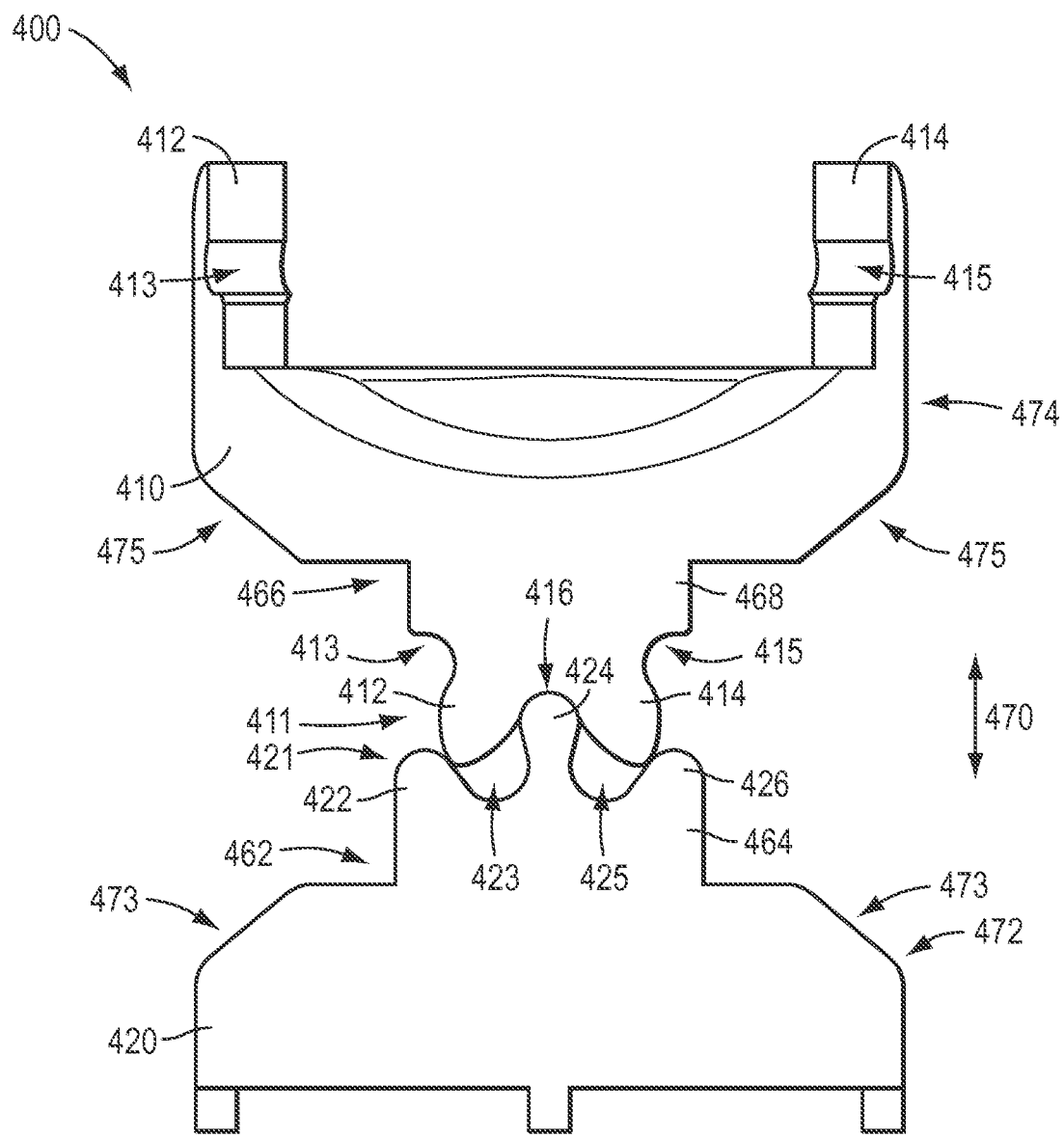
FIG. 3 is a side view of an exemplary embodiment of a joint that includes a plurality of teeth.

Turning to FIG. 3, an exemplary embodiment of a joint 400 for a wrist of a surgical instrument is shown. Joint 400 includes a first disc 410 and a second disc 420, as shown in FIG. 3. Thus, according to an exemplary embodiment, joint 400 may be a two-piece joint in which first disc 410 and second disc 420 are directly in contact with one another. For instance, discs 410, 420 may be in direct contact without additional joint components interposed between discs 410, 420. The term "disc" is used in a general sense as the term is often used in describing a vertebra-like structure. Those having ordinary skill in the art will appreciate that the disc components of the joints can have various shapes and configurations not limited to circular cross-sections or annular shapes.

In contrast with joint members that include only a single tooth and corresponding aperture, such as members 110, 120 of U.S. Pub. No. US 2011/0152879, joint 400 may include discs 410, 420 with respective joint features 411, 421 that intermesh with one another. For instance, joint feature 411 of first disc 410 may include a first tooth 412 and a second tooth 414, as shown in the exemplary embodiment of FIG. 3, although other numbers of teeth may be utilized, such as, for example, three, four, or more teeth. Joint feature 421 of second disc 420 may include a first pin 422, a second pin 424, and a third pin 426 configured to engage with teeth 412, 414, as shown in FIG. 3, although other numbers of pins may be utilized, such as, for example, four, five, or more pins. Pins 422, 424, 426 may each have a constant radius of curvature, according to an exemplary embodiment. The radius of curvature of a pin may differ from an adjacent portion of a disc. As a result, pins may differ in diameter from one another.

Figure 11A:
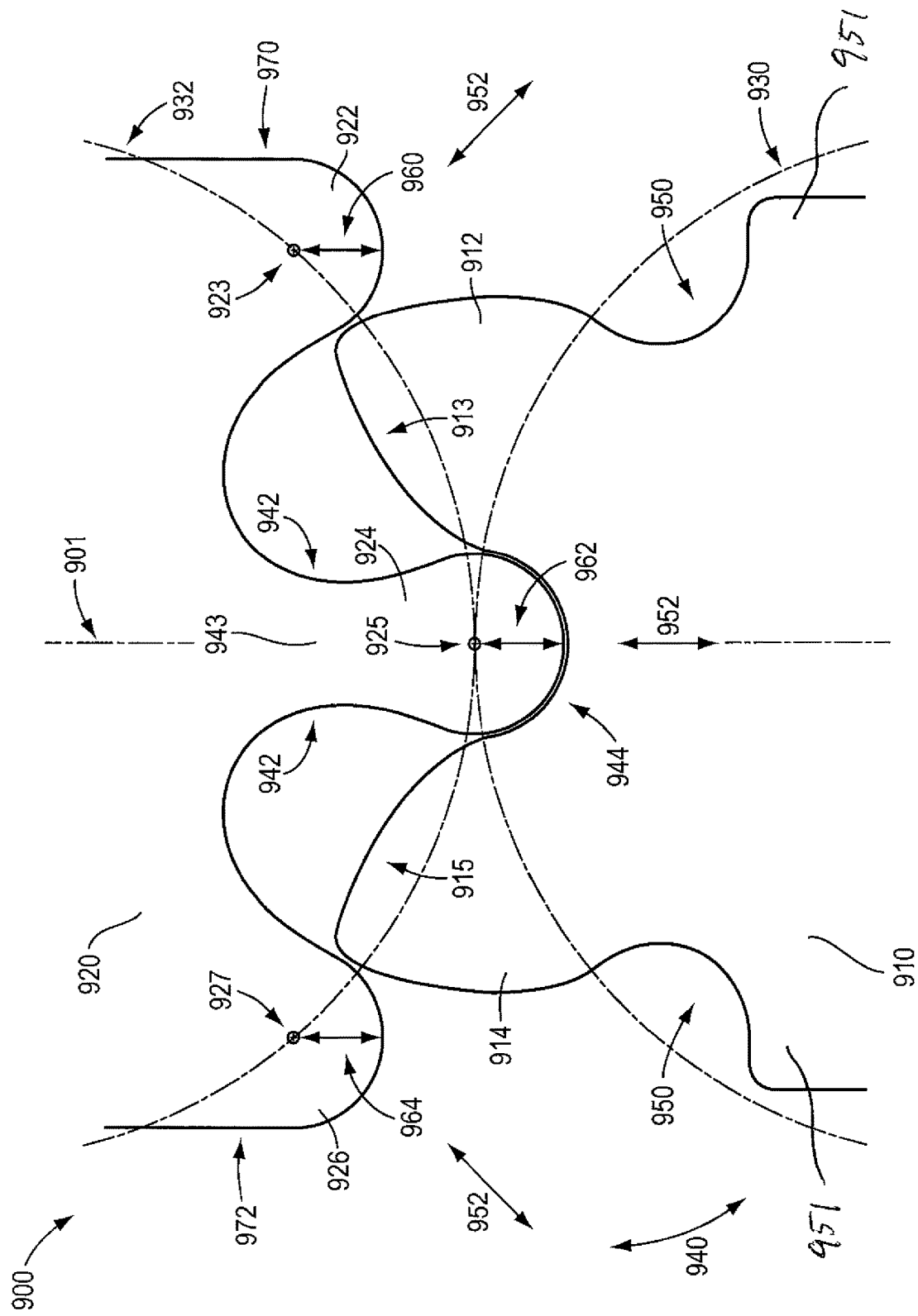
FIG. 11A is a side, detailed view of an exemplary embodiment of a joint that includes pins located on a circular arc projected onto a plane of the pins.

The radius of curvature of a pin is demonstrated in the exemplary embodiment of FIG. 11A, which shows a disc 940 including pins 922, 924, 926 having respective radii of curvature 960, 962, 964 with respect to their pin centers 923, 925, 927. As shown in the exemplary embodiment of FIG. 11A, disc portions 970, 972 adjacent to pins 922, 926 have different radii of curvature, and therefore a different shape, than pins 922, 926. Similarly, stem 943 adjacent to pin 924 has a different radius of curvature, and therefore a different shape, than pin 924. Further, although each pin 922, 924, 926 have the same radius of curvature, 960, 962, 964, the radii 960, 962, 964 may differ from one another. For instance, each radii 960, 962, 964 may be different or at least one of radii 960, 962, 964 may differ from the others. In one example, radii 960 and 964 may be the same but radius 962 may differ.

Figure 16:
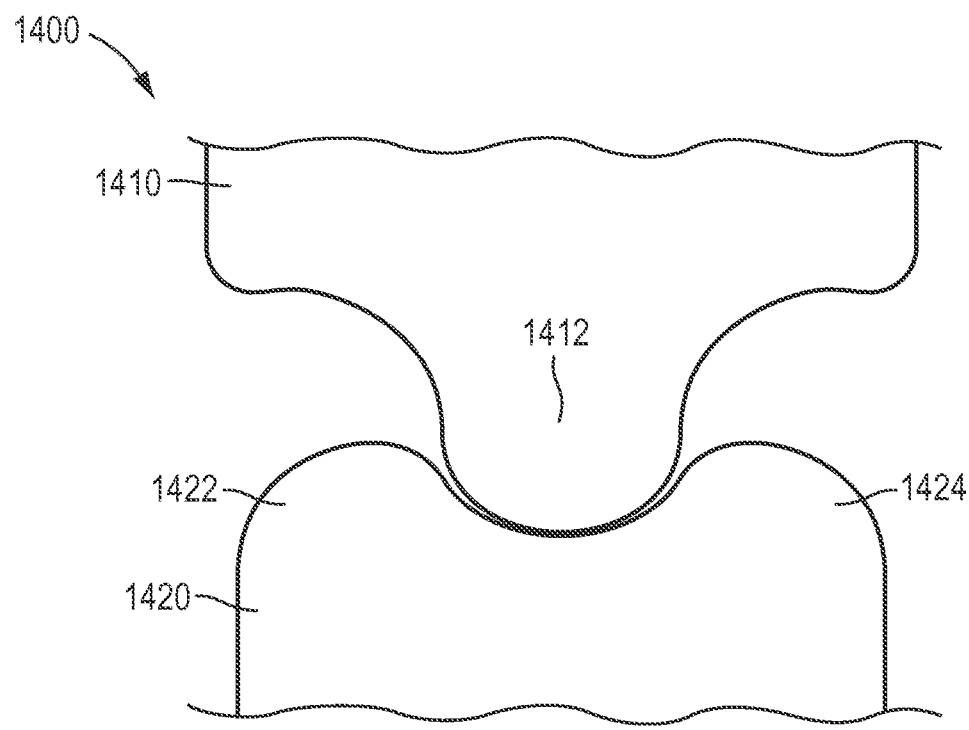
FIG. 16 is a side view of an exemplary embodiment of joint features that have cycloidal surfaces.
Figure 17:
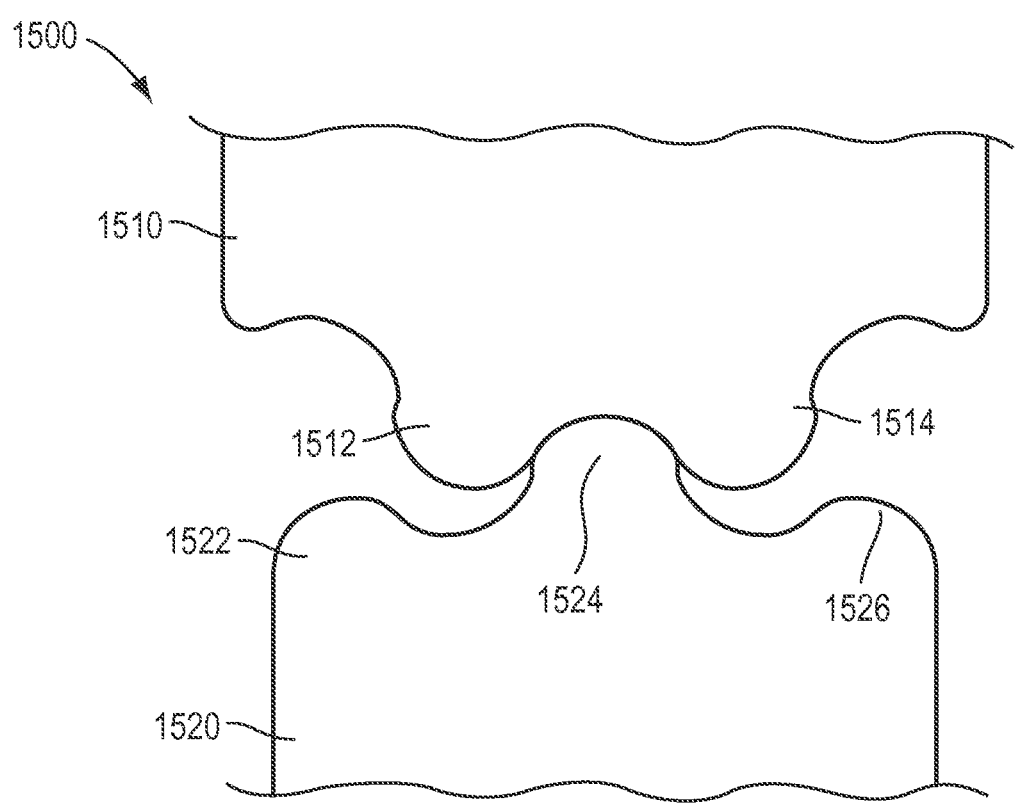
FIG. 17 is a side view of an exemplary embodiment of joint features that have cycloidal surfaces.
Figure 18:
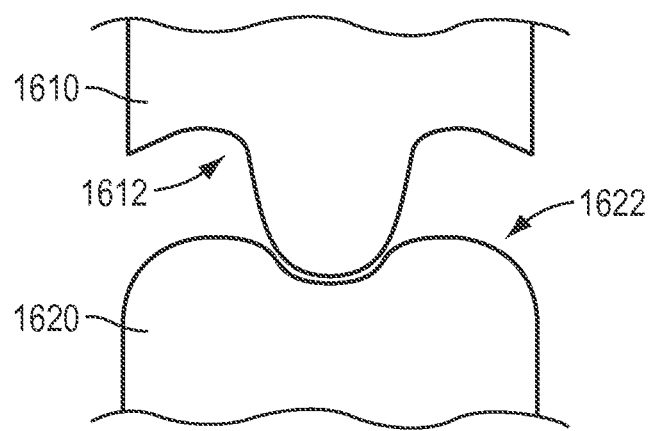
FIG. 18 is a side view of an exemplary embodiment of bearing projections with surfaces having cycloidal shapes.

According to an exemplary embodiment, teeth and pins may have cycloidal shapes, which are described in U.S. Pub. No. US 2011/0152879, incorporated by reference herein. Turning to FIG. 16, an exemplary embodiment of a joint 1400 is shown that includes a disc 1410 having a tooth 1412 having a cycloidal shape and a disc 1420 having pins 1422, 1424 with cycloidal shapes. However, discs of a joint are not limited to a single tooth and two pins but instead may include two, three, or more teeth with cycloidal shapes and three, four, or more pins with cycloidal shapes. For instance, the exemplary embodiment of FIG. 17 depicts a joint 1500 that includes a disc 1510 having two teeth 1512, 1514 with cycloidal shapes and a disc 1520 including pins 1522, 1524, 1526 with cycloidal shapes.

According to an exemplary embodiment, disc 410 may include the plurality of teeth at each end of disc 410 with regard to a proximal-distal direction 470, as shown in FIG. 3. Similarly, disc 420 may include the plurality of pins at each end of disc 420 with regard to the proximal-distal direction 470. In various exemplary embodiments, when a disc includes joint features, which may be a plurality of teeth or pins at each of its ends or a plurality of teeth at one end and a plurality of pins at the other end, the teeth or pins at the opposite ends may be offset from one another by approximately 90 degrees in a circumferential direction, as shown in the exemplary embodiment of FIG. 3.

Figure 4:
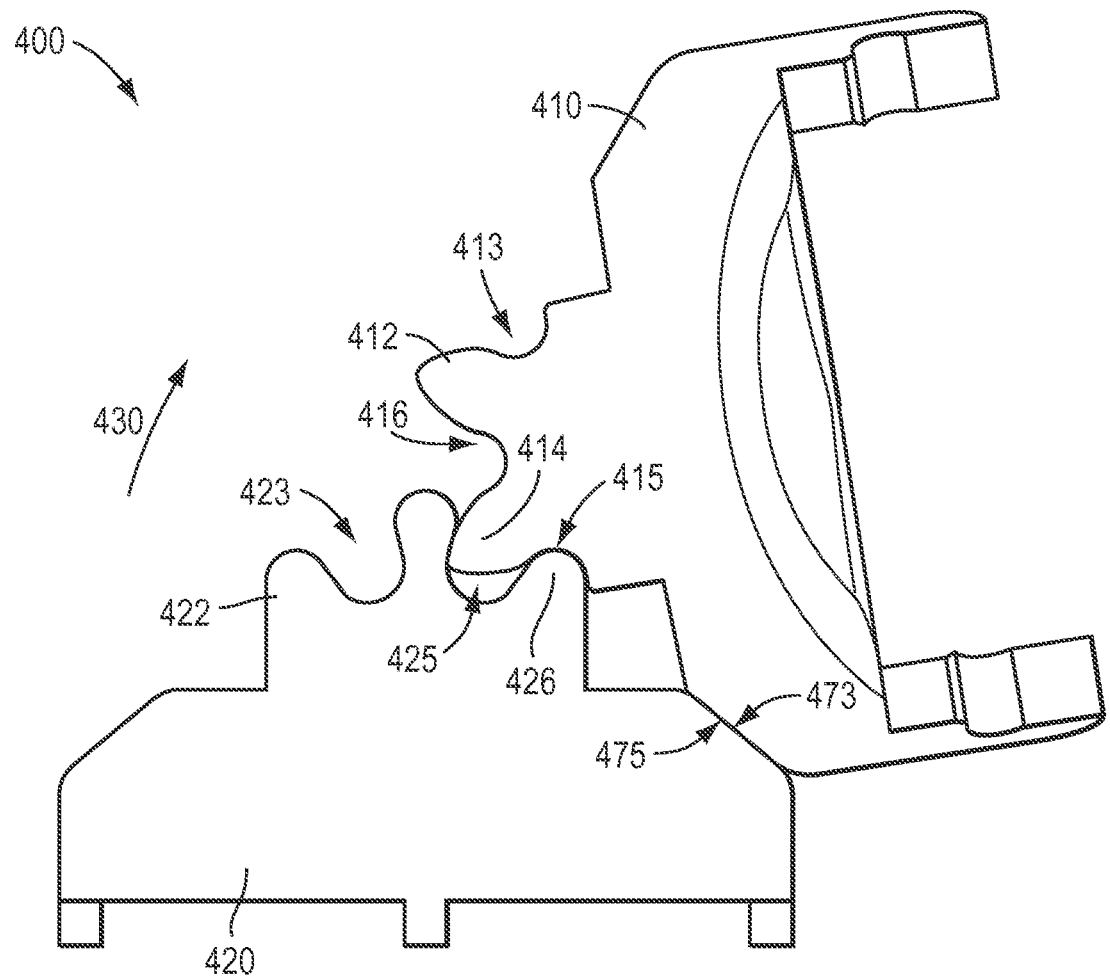
FIG. 4 shows the joint of FIG. 3 after discs of the joint have been rotated relative to one another.

Because joint 400 includes at least one disc with a plurality of teeth, joint 400 provides an enhanced range of motion between first disc 410 and second disc 420. For instance, joint 400 may provide a maximum range of motion (up to a roll angle limit) of greater than +/−45 degrees between first disc 410 and second disc 420, such as, for example, when discs 410, 420 are rotated relative to one another in direction 430, such as for an arbitrary pitch or yaw motion, as shown in FIG. 4. According to another example, joint 400 may provide a maximum range of motion of more than about +/−45 degrees to about +/−75 degrees between first disc 410 and second disc 420. According to another example, joint 400 may provide a maximum range of motion of more than +/−45 degrees to about +/−80 degrees between first disc 410 and second disc 420. According to another example, joint 400 may provide a maximum range of motion of more than +/−75 degrees to about +/−90 degrees between first disc 410 and second disc 420. According to another example, joint 400 may provide a maximum range of motion of about +/−60 degrees to about +/−80 degrees between first disc 410 and second disc 420. Joint 400 may provide even greater ranges of motion between discs 410, 420, such as a maximum range of motion (roll angle limit) of more than +/−45 degrees to about +/−90 degrees between first disc 410 and second disc 420, or a maximum range of motion of about +/−60 degrees to about +/−90 degrees between first disc 410 and second disc 420, although even higher ranges of motion (roll angle limits) between discs 410, 420 may be accomplished.

Figure 15:
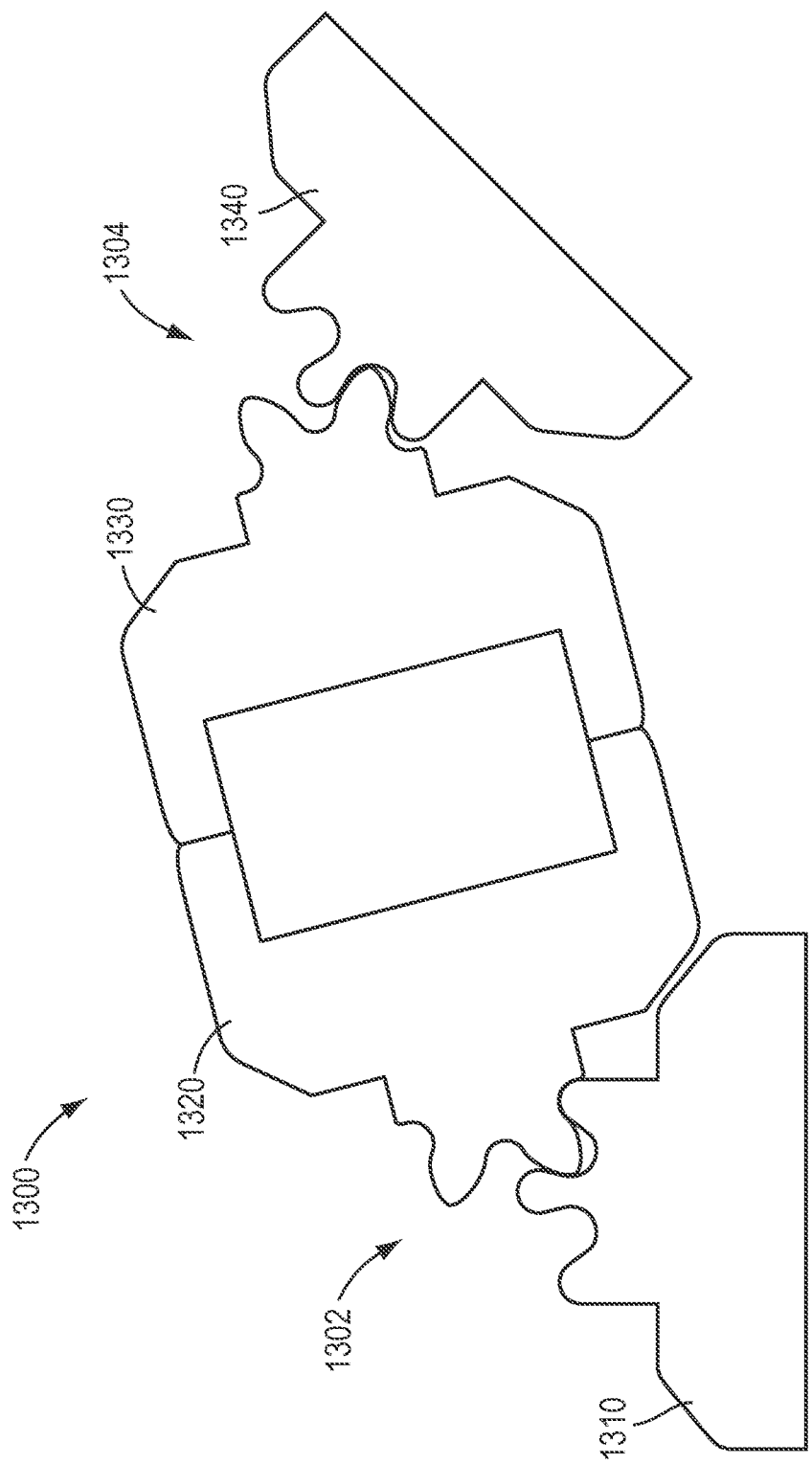
FIG. 15 is a side view of an exemplary embodiment of a wrist including a plurality of joints.

Due to the enhanced range of motion provided by joint 400, a wrist including joint 400 may provide a desired amount of motion, such as +/−90 degrees in a pitch or yaw direction, in a more efficient manner with fewer parts. In previous wrist structures in which each joint is limited to a maximum roll angle of about 45 degrees, several such joints in series are needed to relatively large roll angle for the entire wrist mechanism. But, in accordance with aspects of the invention, fewer joints (and thus discs) may be required to achieve a relatively large range of motion in structures where each joint has a more limited range of motion than the overall range of motion for the structures. And as illustrated, a single joint can provide up to a 90-degree roll angle limit, so that two joints with a 45-degree roll angle limit are needed to achieve the same roll angle. In addition, the single-joint implementation has a shorter end effector throw distance from the centerline of the instrument shaft to the end effector tip, which allows better end effector access in small surgical sites. As a result, a manufacturing cost and complexity for a wrist that includes one or more joints 400 may be reduced while still achieving desired control over articulation. In addition, the plurality of teeth and corresponding plurality of pins included in discs 410, 420 of joint 400 can provide enhanced timing to assist with accurately positioning discs 410, 420, including, for example, returning discs to a neutral position (e.g., zero angle roll alignment), and to enhance smoothness of the motion between discs 410, 420, such as when discs 410, 420 are rotated in direction 430 relative to one another. In addition, the single-joint implementation has a shorter end effector throw distance from the centerline of the instrument shaft to the end effector tip, which allows better end effector access in small surgical sites. According to an exemplary embodiment, a wrist may include a plurality of joints 400 to achieve higher ranges of motion (up to roll limit angles), such as, for example, wrists having a range of motion of up to +/−180 in a pitch or yaw direction. As shown in the exemplary embodiment of FIG. 15, a wrist 1300 may include a first joint 1302 including a first disc 1310 and a second disc 1320 and a second joint 1304 including a third disc 1330 and a fourth disc 1340 to achieve higher ranges of motion.

Joint features also may include other configurations to assist with how teeth and pins of the joint engage with one another. According to an exemplary embodiment, a recess 416 may be provided between teeth 412, 414 of disc 410, with recess 416 shaped to receive a central pin 424 of disc 420, as shown in FIGS. 3 and 4. Further, joint features 421 of disc 420 may include recesses to receive the teeth 412, 414. For example, a recess 423 may be located between pins 422, 424 to receive tooth 412 and a recess 425 may be located between pins 424, 426 to receive tooth 414, as shown in FIGS. 3 and 4. Providing recess 416 to receive pin 424 and recesses 423, 425 to receive teeth 412, 414 may permit closer coupling of teeth 412, 414 and pins 422, 424, 426, such as to permit teeth 412, 414 and pins 422, 424, 426 to extend further between each other. As a result, motion between discs 410, 412 may be made even smoother and the timing of joint 400 may be enhanced. For instance, the ability of discs 410, 412 to substantially return to the straight configuration shown in the exemplary embodiment of FIG. 3 after being rotated relative to one another, as shown in the exemplary embodiment of FIG. 4, may be enhanced, which in turn enhances the ability of a wrist including joint 400 to repeat the rotation shown in FIG. 4 in substantially the same manner, for example, over multiple cycles.

According to an exemplary embodiment, pin recesses 413, 415 also may be provided in locations lateral to or outside teeth 412, 414, as shown in FIGS. 3 and 4. Pin recesses 413, 415 may be configured to receive pins 422, 426 when discs 410, 412 are rotated relative to one another, as illustrated in FIG. 4 (with recess 415 receiving pin 426). As a result, pin recesses 413, 415 may also assist with enhancing engagement between teeth 412, 414 and pins 422, 424, 426 (in other words to maintain tooth 414 in the recess between the pins 426, 424 as depicted in FIG. 4), even when discs 410, 412 are rotated relative to one another at relatively high ranges of motion, such as up to about +/−75 degrees or more, for example.

According to an exemplary embodiment, joint members that include a plurality of teeth may have at least one of the teeth become disengaged with corresponding pins during articulation of a joint. Intermesh and engage, as used herein when discussing joint features, such as teeth and pins, does not necessarily mean that joint features are in contact. As will be discussed below, joint features, such as teeth and pins, may be spaced apart from one another and not in contact during normal conditions, or joint features may be in contact with one another under normal conditions, such as to provide surfaces that bear a compressive load. For example, when intermeshed or engaged teeth and pins are not normally in contact during normal conditions, teeth and pins may subsequently come into contact with one another, such as when a lateral force and/or a torque causes discs to shift relative to one another in a lateral direction. Teeth and pins may also contact one another when discs shift relative to one another along a longitudinal direction, particularly when discs are already rotated relative to one another. When this occurs, a gap between at least one tooth and one or more pins closes, causing the intermeshed tooth and the pin(s) to contact one another, which substantially prevents further lateral movement between the discs and potential dislocation of the joint. As a result, the relative positions of the discs may be maintained, which enhances the timing of a joint including the discs and the minimization or elimination of the degree of freedom for movement of discs in a lateral direction, even when intermeshed or engaged joint features do not normally contact one another. In another example, intermeshed or engaged teeth and pins may be normally in contact with one another, such as when teeth and pins themselves serve as load bearing surfaces. For instance, in the exemplary embodiments of FIGS. 16 and 17, teeth 1412, 1512, 1514 and pins 1422, 1424, 1522, 1524, 1526 may themselves serve as load bearing surfaces without additional load bearing projections.

FIG. 3 shows an exemplary embodiment of teeth and pins engaged in a neutral state of the joint 400, with tooth 412 intermeshed with pins 422 and 424 and tooth 414 intermeshed with pins 424 and 426. Further, pin 424 may be received in pin recess 416 and teeth 412, 414 may be at least partially received in and located at outer edges of tooth recesses 423, 425, respectively. When discs 410, 420 are rotated in direction 430, as shown in the exemplary embodiment of FIG. 4, the rotation can result in tooth 412 disengaging from corresponding pins 422, 424 and being removed from the tooth recess 423. However, in the position of FIG. 4, when at least one tooth becomes disengaged due to relative rotation of discs, another tooth may remain engaged with corresponding pins so that the teeth and pins may continue to affect the positioning and timing of discs 410, 420. For instance, when discs 410, 420 are rotated relative to one another in direction 430, tooth 414 may remain engaged with pins 424 and 426. Further, a majority of tooth 414 is received in tooth recess 425, as shown in FIG. 4.

Figure 5:
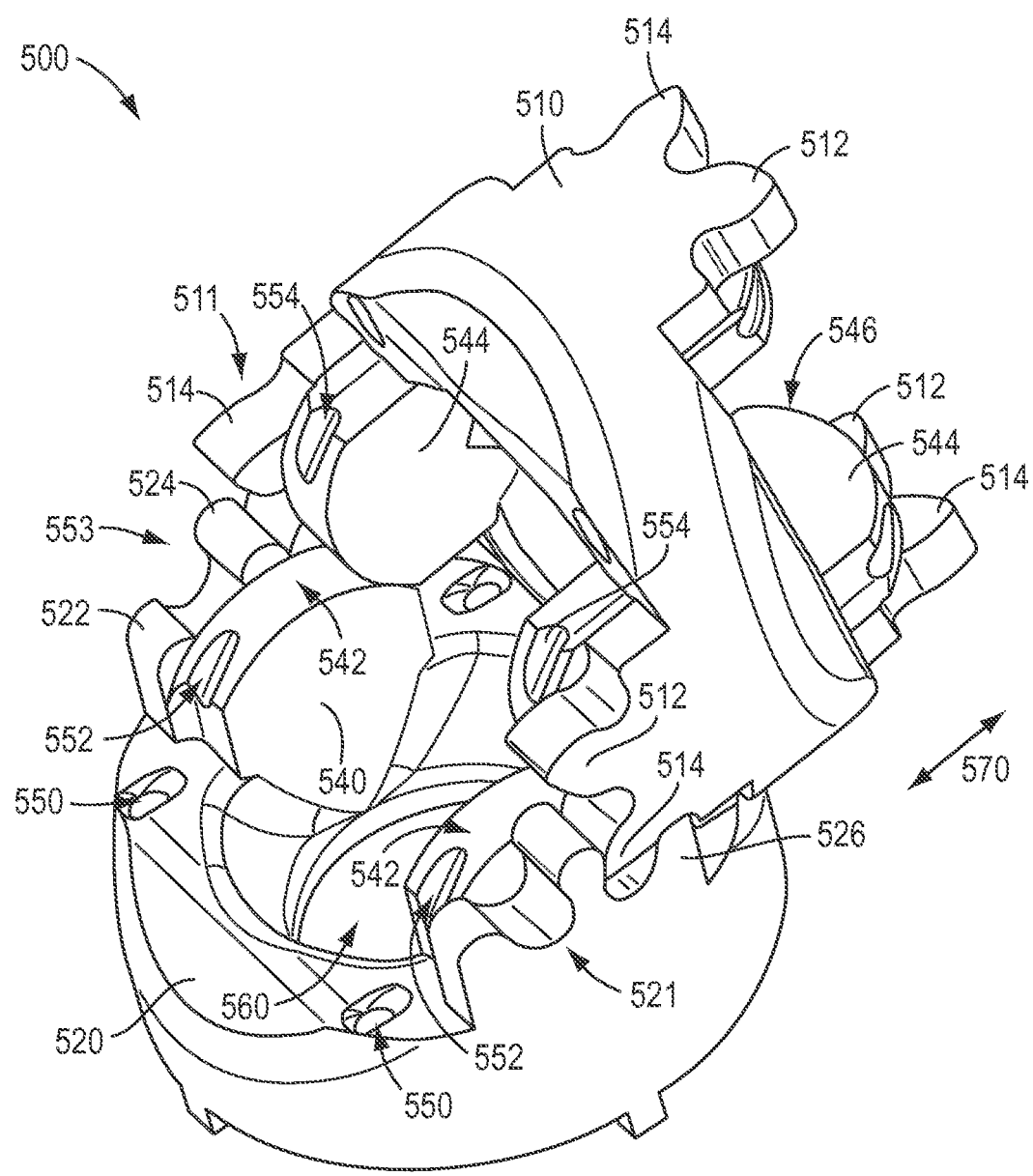
FIG. 5 shows a perspective view of an exemplary embodiment of a joint that includes bearing projections.

As discussed above, a joint 400 including discs 410, 420 may be provided in a wrist of a surgical instrument, such as wrist 220 in the exemplary embodiment of FIG. 2. When used in a wrist of a surgical instrument, discs 410, 420 may be pulled together by drive tendon (not shown), which may be used to control the motion of joint 400, as discussed above for the exemplary embodiment of FIG. 1, and to press discs 410, 420 against one another to hold the components of the wrist together, as those having ordinary skill in the art are familiar with. According to an exemplary embodiment, disc 510 may include one or more tendon passages 554 to accommodate a corresponding number of tendons passing through disc 510, as shown in FIG. 5. Similarly, disc 520 may include one or more tendon passages 550. According to an exemplary embodiment, a disc may include more than one passage for each tendon, such as when separate portions of the disc lie in an intended path of a tendon. For instance, disc 520 may include tendon passage 550 and another tendon passage 552 for the same tendon in another part of disc 520. According to an exemplary embodiment, passages 550, 552 are not aligned with one another along a direction extending substantially parallel to a longitudinal axis of joint 500. Tendon passages 550, 552, 554 of the exemplary embodiment of FIG. 5 may have a larger diameter than the diameter of a tendon to permit the tendon to move back and forth within the passages when discs 510, 520 are rotated relative to one another, according to an exemplary embodiment. According to an exemplary embodiment, a disc may include two tendon passages (such as when push/pull actuation members are utilized), three tendon passages, four tendon passages, or a higher number of tendon passages.

A consequence of a configuration in which tendons hold discs of a joint together is that a compressive load is applied between the discs. To address these compressive loads, exemplary joint members may include one or more joint features comprising load bearing surfaces to accommodate the compressive load. FIG. 5 illustrates another exemplary embodiment of a joint having similar elements as the exemplary embodiment of FIGS. 3 and 4 but with additional joint features. For instance, disc 510 may include one or more bearing projections 544 having a load bearing surface 546 configured to receive a load, such as a compressive load, and disc 520 may include one or more bearing projections 540 having a load bearing surface 542 configured to receive the compressive load, such as by engaging with surface 546 of projection 544, as shown in FIG. 5. According to an exemplary embodiment, surfaces 542, 546 may be configured to remain in contact with one another throughout motion of discs 510, 520 relative to one another as long as a compressive load is applied between discs 510, 520.

Figure 19:
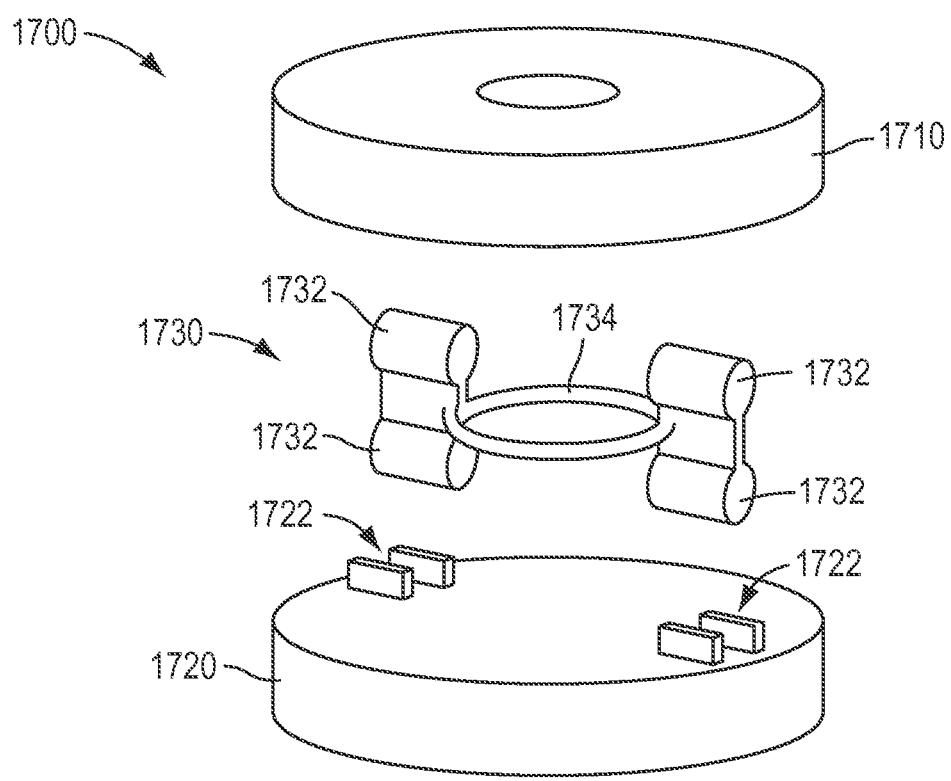
FIG. 19 is an exploded perspective view of an exemplary embodiment of a joint that includes a strut.

As shown in the exemplary embodiment of FIG. 5, surfaces 542, 546 of bearing projections 540, 544 may have the shape of a partial cylinder. However, the surfaces of the bearing projections of the exemplary embodiments described herein are not limited to partial cylinders and may instead have other shapes. According to an exemplary embodiment, bearing projections may have surfaces with cycloidal shapes, as described in U.S. Pub. No. 2011/0152879. For instance, a first bearing projection 1610 may have a surface 1612 with a cycloidal shape and a second bearing projection 1620 may have a surface 1622 with a cycloidal shape, as described in U.S. Pub. No. 2011/0152879. According to another exemplary embodiment, bearing projections may be provided by struts, as described in the exemplary embodiments of U.S. Pat. No. 6,817,974, published on Nov. 16, 2004, which is hereby incorporated by reference in its entirety. A strut may be provided as a separate piece connecting two adjacent discs, as described in U.S. Pat. No. 6,817,974, thus providing a three-piece joint. For instance, as shown in the exemplary embodiment of FIG. 19, a joint 1700 may include a first disc 1710 and a second disc 1720 (each shown schematically in FIG. 19) and a strut 1730 configured to connect and bear the load between discs 1710 and 1720. As shown in the exemplary embodiment of FIG. 19, strut 1730 may include projections 1732 and a ring 1734 connecting projections 1732. Each of discs 1710 and 1720 may include features to engage projections 1732 to connect discs 1710 and 1720 via strut 1730, such as, for example, grooves 1722 in disc 1720.

According to an exemplary embodiment, disc 510 may include a bearing projection 544 at each end of disc 510 with regard to the proximal-distal direction 570 shown in FIG. 5. Similarly, disc 520 may include a bearing projection 540 at each end of disc 520. When a disc includes a bearing projection at each of its ends, the projections at the opposite ends may be offset from one another by approximately 90 degrees in a circumferential direction, as shown in the exemplary embodiment of FIG. 5. However, bearing projections are not limited to the configuration shown in FIG. 5 and instead may have positions in which bearing projections are substantially aligned along a longitudinal axis of discs instead of being offset from one another, such as to increase the range of motion of a wrist including the discs.

According to an exemplary embodiment, the bearing projections 540 and 544 may be separate from joint features 511, 521 that include the teeth 512, 514 and pins 522, 524, 526, respectively. For instance, bearing projection 540 may be a physically separate, distinct member from pins 522, 524, 526, as shown in FIG. 5. Surface 542 of projection 540 may be a separate, distinct surface from surfaces provided by pins 522, 524, 526. In addition, bearing projection 544 and bearing surface 546 may be a physically separate, distinct member from teeth 512, 514, as shown in FIG. 5, and surface 546 of projection 544 may be a separate, distinct surface from surfaces provided by teeth 512, 514. According to an exemplary embodiment, projections 540, 544 may be located in a different radial location than pins 522, 524, 526 and teeth 512, 514 with respect to a central aperture 560 of disc 520 through which various control tendons, rod, and other instrument components may pass. According to an exemplary embodiment, bearing projection 540 may be located radially inward so that bearing projection 540 is located closer to central aperture 560 of disc 520 than joint feature 521, which may include pins 522, 524, 526, as shown in FIG. 5. Similarly, bearing projection 544 may be located radially inward so that bearing projection 540 is located closer to central aperture (not shown) of disc 510 than joint feature 511, which may include teeth 512, 514.

Although teeth 512, 514 and pins 522, 524, 526 and bearing projections 540, 544 may be a part of discs 510, 520 (i.e., have a one-piece construction with discs 510, 520), teeth 512, 514 and pins 522, 524, 526 and bearing projections 540, 544 are not limited to such a configuration. For example, teeth 512, 514 and/or pins 522, 524, 526 and/or bearing projections 540, 544 may instead be provided as separate pieces connected to discs 510, 520.

As noted above, teeth and pins of discs may be spaced apart from one another during normal conditions, even when teeth 512, 514 are engaged with pins 522, 524, 526, as shown in the exemplary embodiment of FIG. 5. For instance, a gap of about 0.001" may be provided between teeth 512, 514 and corresponding pins 522, 524, 526 under normal conditions, such as when joint 500 is not subjected to a lateral force and/or torque. In such a configuration, projections 540, 544 may be used to bear compressive loads between discs 510, 520 because teeth 512, 514 and pins 522, 524, 526 may not be in contact to bear compressive loads. According to another embodiment, teeth 412, 414 and pins 422, 424, 426 of the joint 400 of FIG. 3 may be in contact with one another when teeth 412, 414 and pins 422, 424, 426 are engaged. As a result, teeth 412, 414 and pins 422, 424, 426 may serve as bearing surfaces for a compressive load. In a configuration in which teeth and pins act as bearing surfaces, bearing projections may be omitted as load bearing surfaces, according to an exemplary embodiment, due to the teeth and pins acting as load bearing surfaces. As noted above, teeth 1412, 1512, 1514 and pins 1422, 1424, 1522, 1524, 1526 in the exemplary embodiments of FIGS. 16 and 17 may themselves serve as load bearing surfaces without additional load bearing projections.

Joint members may include various other design features other than those discussed in the exemplary embodiments above. For instance, with reference to FIGS. 3 and 4, joint feature 421 of disc 420 may form a shoulder 462 relative to a body 472 of disc 420 and joint feature 411 of disc 410 may include a projection 468 that forms a shoulder 466 relative to a body 474 of disc 410, as shown in the exemplary embodiment of FIGS. 3 and 4. For instance, joint feature 421 may be located on a projection 464 that forms shoulder 462 relative to a body 472 of disc 420 and joint feature 411 may be located on a projection 468 that forms shoulder 466 relative to body 474 of disc 410. Shoulders 462, 466 may form an approximate right angle relative to body 472, 474. Bodies 472, 474 of discs 420, 410 may respectively include sloped surfaces 473, 475 that may engage one another when discs 420, 410 are rotated relative to one another to the limit of the range of motion between discs 420, 410, as shown in FIGS. 3 and 4. Thus, sloped surfaces 473, 475 may serve as stops limiting rotation between discs 410, 420.

Also, teeth and/or tooth recesses may be relatively large and configured to provide a large degree of surface contact when intermeshed. In contrast to the use of a larger number of small teeth which can be more easily disengaged by a side load, this large surface contact can assist to minimize slippage between discs, such as under relatively high side loads. The large surface contact also minimizes rotation (in contrast to roll) between discs such as rotation about a longitudinal axis of a joint. Thus by minimizing slippage between the bearing surfaces of the discs, and relative axial rotation of the discs, the wrist can be used at large angles (e.g., more than 45 degrees and up to 90-degrees, depending on the roll angle limit of an individual configuration) without the two discs disengaging from one another under loads experienced during surgery.

Figure 6:
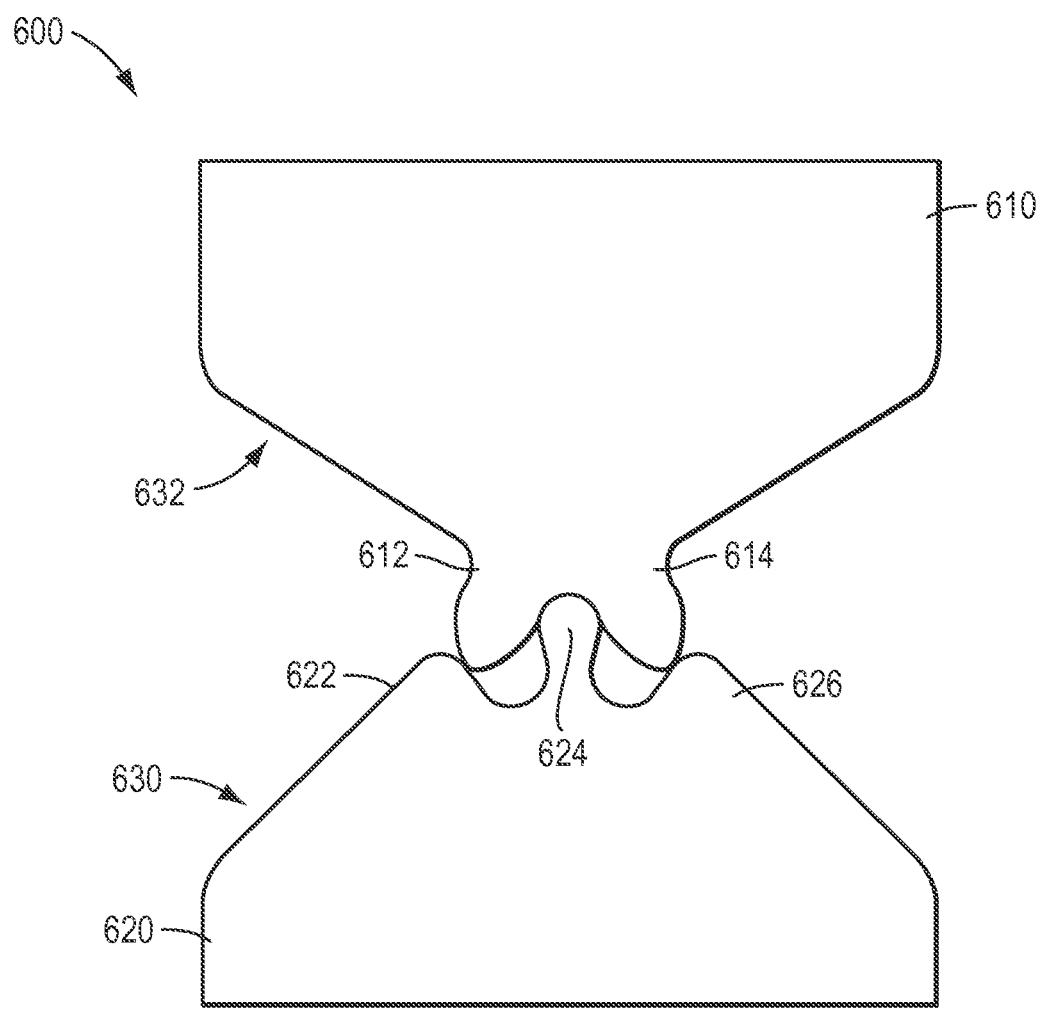
FIG. 6 is a side view of an exemplary embodiment of a joint that includes discs lacking shoulders.

According to another exemplary embodiment, a joint 600 may include discs 610, 620 that do not have shoulders or projections from a disc body that form a shoulder, as shown in FIG. 6. Disc 610 may include teeth 612, 614 that extend from a sloped surface 632 on the side of disc 610 instead of a shoulder. Similarly, disc 620 may include pins 622, 624, 626 that extend from a sloped surface 630 on the side of disc 620. For instance, teeth 612, 614 may extend directly from sloped surface 632 and pins 622, 624, 626 may extend directly from sloped surface 630. Discs 610, 620 may include other features discussed above for the discs 410, 420 of the exemplary embodiments of FIGS. 3 and 5, such as projections 540, 544 and recesses 413, 415, 416, 423, 425.

As shown and discussed above with reference to the exemplary embodiment of FIG. 5, bearing projections 540, 544 of discs 520, 510 may be located closer to central aperture 560 than pins 522, 524, 526 and teeth 512, 514 along a radial direction, respectively. Such a configuration may lead to openings 553 between teeth 512, 514 and pins 522, 524, 526 when discs 510, 520 are rotated relative to one another, as shown in FIG. 5. If joint 500 is used in a wrist or other component of a surgical instrument where discs 510, 520 are exposed to a surrounding environment, it may be desirable to design discs 510, 520 to minimize or eliminate openings between teeth 512, 514 and pins 522, 524, 526, even for relatively large rotation of the discs 510, 520. For instance, openings 553 between teeth and pins may permit materials from the surrounding environment to enter in opening 553, which can potentially hinder articulation of the joint.

Figure 7:
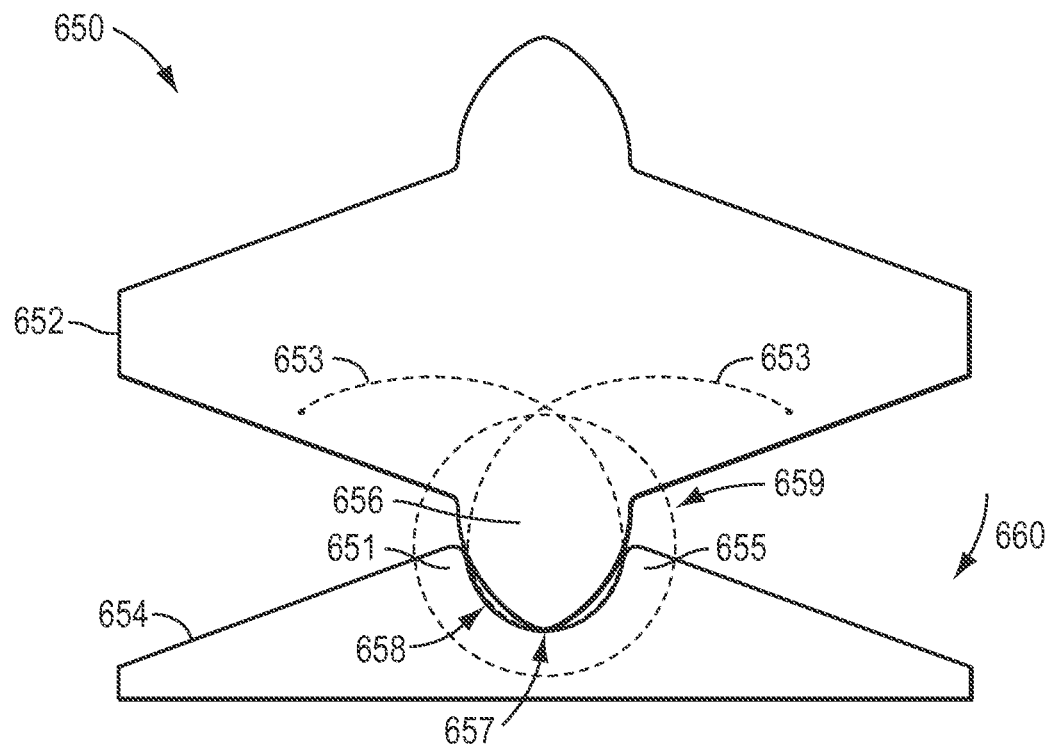
FIG. 7 is a side view of an exemplary embodiment of a joint that includes a recess having a trochoid surface.

Turning to FIG. 7, an exemplary embodiment of a joint 650 is shown that includes a first disc 652 and a second disc 654. Disc 652 may include a tooth 656 and disc 654 may include pins 651, 655. According to an exemplary embodiment, a recess 658 of disc 654 configured to accommodate tooth 656 may have a trochoid shape to minimize or eliminate openings between teeth and pins. As shown in the exemplary embodiment of FIG. 7, tip 657 of tooth 656 may trace a curve 653 as first disc 652 and second disc 654 are rotated relative to one another, with the ends of curve 653 extended beyond the physical range of motion limits between discs 652, 654 so that the shape of curve 653 is more apparent. By using a recess 658 with a trochoid surface in a joint 650, an opening between tooth 656 and recess 658 can be minimized or eliminated, particularly when joint 650 includes a single tooth 656. When a joint includes multiple teeth, such as in the exemplary embodiments of FIGS. 3-5, a gap or other misalignment may still occur between the teeth and pins, particularly when the joint is actuated to large ranges of motion.

Figure 8:
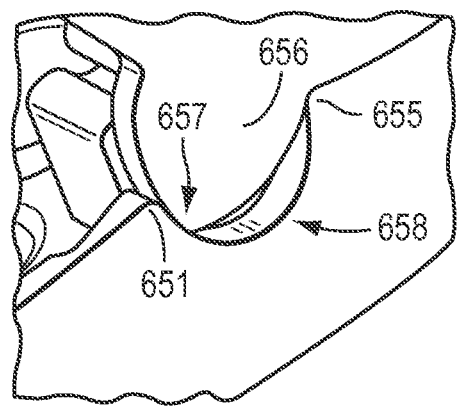
FIG. 8 is a partial detailed view of the joint of FIG. 7 after discs of the joint have rotated relative to one another.

Turning to FIG. 8, which shows an enlarged view of area 659 after discs 652, 654 have been rotated relative to one another in direction 660 in FIG. 7 to their fullest extent, tooth 656 remains engaged with a surface of recess 658. For instance, tip 657 of tooth 656 may remain received within recess 658, as shown in FIG. 8, particularly when joint 650 includes a small number of teeth. Further, a gap between tooth 656 and pins 651, 655 (and also between tooth 656 and the surface of recess 658) may remain small, such as when tooth 656 and pins 651, 655 do not contact one another under normal conditions (e.g., when no lateral force and/or torque is applied to joint 650), thus minimizing or eliminating openings between tooth 656 and pins 651, 655 in which materials from a surrounding environment could enter when discs 652, 654 rotate back toward a neutral position.

Another method of addressing openings between teeth and pins is to reduce the exposure of openings between teeth and pins to a surrounding environment. In the exemplary embodiment of FIG. 5, bearing projections 540, 544 of discs 520, 510 may be radially inward to pins 522, 524, 526 and teeth 512, 514, respectively, relative to central aperture 560. As a result, teeth 512, 514 and pins 522, 524, 526 are located on a periphery of discs 510, 520 and openings 553 between teeth 512, 514 and pins 522, 524, 526, such as when discs 510, 520 are rotated relative to one another, may be exposed to a surrounding environment. In another exemplary embodiment, bearing projections may be located at a greater radial distance from a central projection than teeth or pins.

Figure 9:
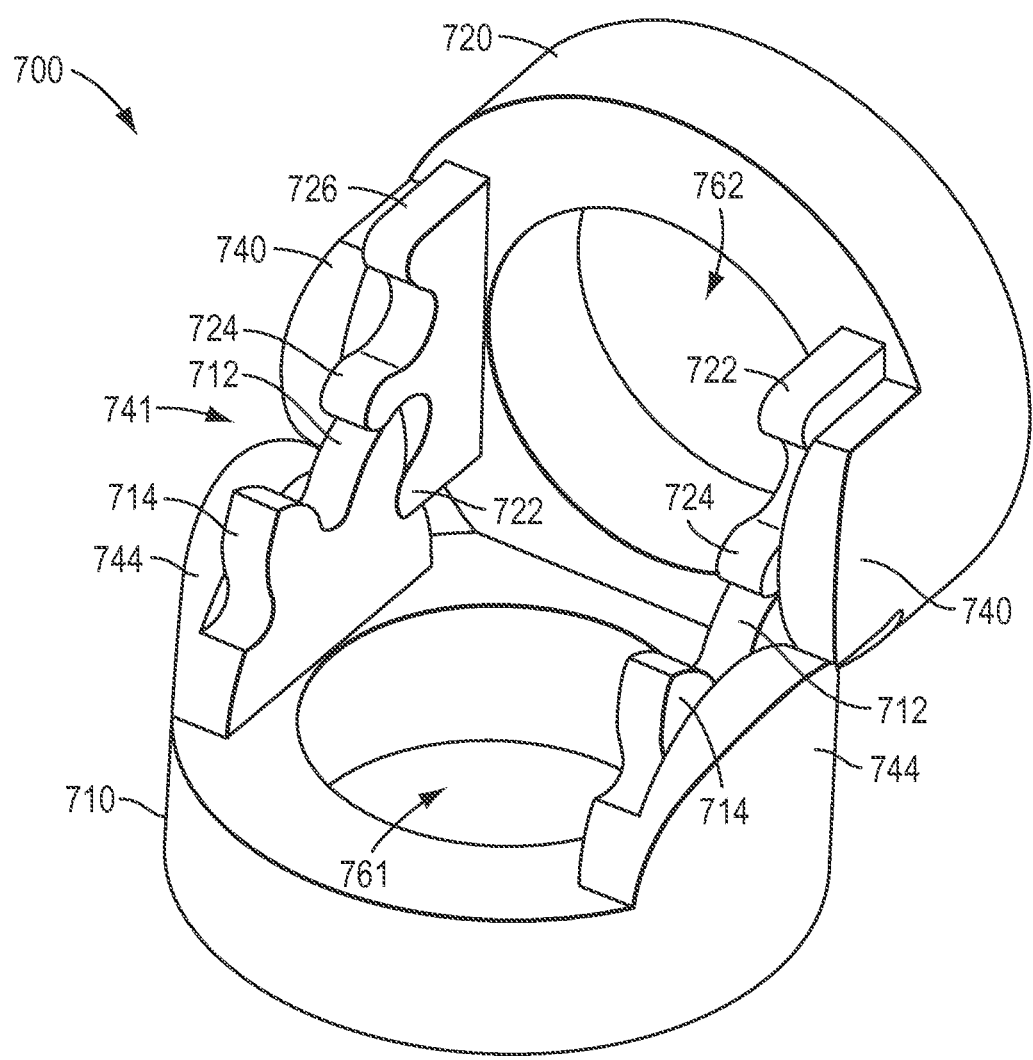
FIG. 9 is a perspective view of an exemplary embodiment of a joint that includes teeth and pins located at a radially inward position.

Turning to FIG. 9, an exemplary embodiment of a joint 700 is shown that includes a first disc 710 and a second disc 720. Disc 710 may include teeth 712, 714 and a bearing projection 744, as described above for the exemplary embodiment of FIG. 5, but with bearing projection 744 at an outboard location relative to teeth 712, 714. For instance, bearing projection 744 may be located at a greater radial distance from central aperture 761 than teeth 712, 714. Disc 720 may include pins 722, 724, 726 and a bearing projection 740, as described above for the exemplary embodiment of FIG. 5, but with bearing projection 740 located at an outboard location relative to pins 722, 724, 726. For instance, bearing projection 740 may be located at a greater radial distance from central aperture 762 of disc 720 than pins 722, 724, 726. As a result, teeth 712, 714 and pins 722, 724, 726 are not located on an outer periphery of discs 710, 720 and bearing projections 740, 744 may shield teeth 712, 714 and pins 722, 724, 726 to a degree so that openings between teeth 712, 714 and pins 722, 724, 726 are less exposed to a surrounding environment in comparison to the exemplary embodiment of FIG. 5.

Figure 10:
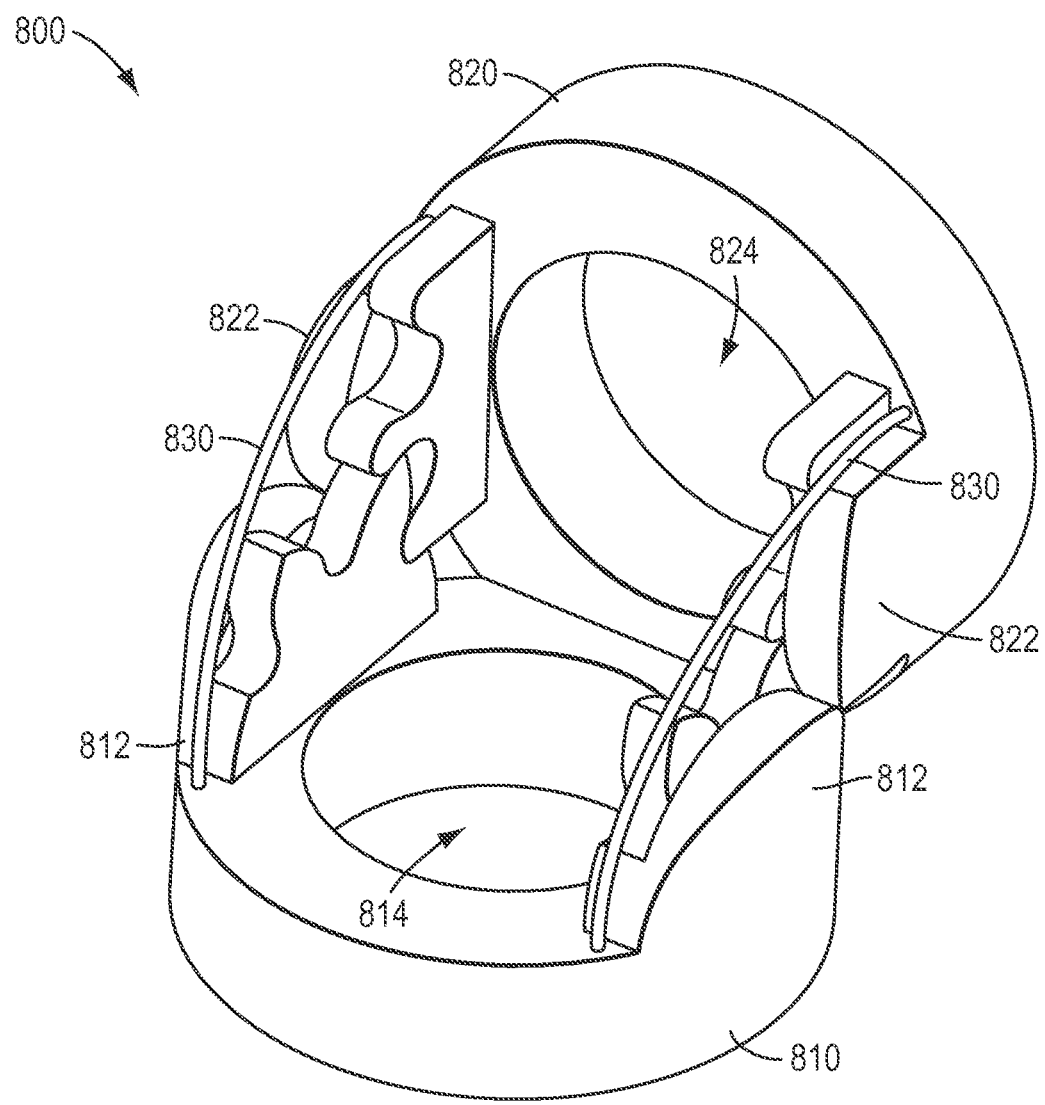
FIG. 10 is a perspective view of an exemplary embodiment of a joint including tendons extending through the joint.

According to an exemplary embodiment, projections 740, 744 of discs 710, 720 may include tendon passages to permit tendons to pass through discs 710, 720, such as tendon passages 550, 552, 554 shown in the exemplary embodiment of FIG. 5. Turning to FIG. 10, an exemplary embodiment of a joint 800 including discs 810, 820 is shown, which may be configured according to the exemplary embodiment of FIG. 9. Discs 810, 820 may respectively include bearing projections 812, 822. Because bearing projections 812, 822 are located at an outboard location relative to central apertures 814, 824 (bearing projections 812, 822 may be located radially outward and proximate to a periphery of discs 810, 820), drive tendons 830 extending through passages in bearing projections 812, 822 also are located at an outboard location. Because drive tendons 830 are located at the periphery of discs 810, 820 and extend between discs 810, 820, tendons 830 can provide a barrier to materials from a surrounding environment and reduce or eliminate the entry of such materials into openings between the teeth and pins of discs 810, 820.

One consideration for disc embodiments that include teeth and pins located at a radially inward location relative to a bearing projection that provides a loading surface is the ease of manufacturing the disc. For instance, positioning the teeth and pins radially inward of the bearing projections can pose manufacturing challenges, such as when molding or machining the discs, in comparison to disc embodiments in which teeth and pins are located at a radially outward location relative to a bearing projection. In view of this consideration, various exemplary embodiments contemplate discs for a joint that are configured to facilitate manufacture of the disc, including, for example, discs that include teeth or pins at an inward radial location relative to a projection and a central aperture.

As shown in FIG. 11A, a joint 900 that includes a first disc 910 having teeth 912, 914 and a second disc 920 having pins 922, 924, 926, according to an exemplary embodiment. The configuration shown in the exemplary embodiment of FIG. 11A may be used in the exemplary embodiments of FIGS. 3-6, 9, and 10. Teeth 912, 914 and pins 922, 924, 926 are configured to engage one another when joint 900 is in the neutral position shown in FIG. 11A and as discs 910, 920 roll relative to one another. Circular arcs (represented by dashed lines) 930, 932 represent contact surfaces (bearing surfaces) between discs 910, 920. Circular arcs 930, 932 represent a rolling surface of motion of the discs, which corresponds to a theoretical arc through the points of contact between the pins and gears. Thus, circular arcs 930, 932 may correspond to contact surfaces (bearing surfaces) between discs 910, 920. For instance, when discs 910, 920 include bearing projections, such as bearing projections 540, 544 of the exemplary embodiment of FIG. 5, and the bearing projections have a shape of a partial cylinder, circular arcs 930, 932 correspond to the cylindrical bearing surface. Circular arcs 930, 932, for instance, may be projections of surfaces of bearing projections 540, 544, 740, 744 discussed above with regard to the exemplary embodiments of FIGS. 5 and 9 onto a plane of pins 922, 924, 926. The plane of pins 922, 924, 926 may be, for example, the plane of the page of FIG. 11A. For instance, circular arcs 930, 932 may follow the contour of the load bearing surface of a bearing projection and indicate the position of pins 922, 924, 926 relative to the load bearing surface (e.g., adjacent the load bearing surface). Thus, circular arcs 930, 932 may trace a load bearing surface of a bearing projection of a respective disc. In other words, although pins 922, 924, 926 may be offset from bearing projections in a radial direction of joint 900, as shown in the exemplary embodiments of FIGS. 5 and 9, centers 923, 925, 926 of pins 922, 924, 926 may extend in direction 952 to substantially the same extent as a bearing projection of disc 920. As a result, discs 910, 920 may roll relative to one another in directions 940 as though discs 910, 920 act as two circles (represented by circular arcs 930, 932) rolling against one another. In particular, the respective centers 923, 925, 927 of pins 922, 924, 926 lie on circular arc 932. For instance, in the neutral position (e.g., at a zero angle roll alignment) shown in FIG. 11A, joint 900 is straight so that a longitudinal axis 901 passes through centers of both of discs 910, 920. Further, when discs 910, 920 are rotated relative to one another in direction 940, centers 923, 925, 927 of pins 922, 924, 926 may remain on circular arc 932 because the distance between pin centers 923, 925, 927 and circular arc 932 does not substantially change.

As shown in FIGS. 11A-E, teeth 912, 913, the recess/depression 944 between the teeth, and the side cutouts/recesses 950 on the opposite sides of each tooth 912,913 act as a mechanical timing feature on the first disc. Similarly, pin/projection 924, the side pins/projections 922, 926, along with the recesses/depressions between the pins/projections 922, 924 and 922, 926 act as a mechanical timing feature on the second disc. In the context of the disclosed embodiments, timing refers to mechanical indexing of motion between the two discs, which are components of a wrist or similar structure, so that the angular roll relation between the two components may be precisely controlled and known after a control input is made to change the angular roll relation to a desired value. Thus, various implementations of such timing features are disclosed.

According to an exemplary embodiment, a joint may be configured to have half of the range of motion of joint 900. For example, a joint may be configured similarly to joint 900 in the exemplary embodiment of FIG. 11A but have only half of the structure of joint 900, such as, for example, only the structures to the left of longitudinal axis 901 or to the right of longitudinal axis 901. Thus, if the joint has only the structures to the left of longitudinal axis 901 in FIG. 11A, the joint may rotate to the left of longitudinal axis 901 along directions 940, with motion stopping when joint is straight (such as discs 910, 920 in FIG. 11A) so that the joint has half of the range of motion of joint 900. Similarly, if the joint has only structure to the right of longitudinal axis 901 in FIG. 11A, the joint may rotate to the right of longitudinal axis 901 along directions 940, with motion stopping when the joint is straight.

To enhance the timing of joint 900 and the smoothness of motion of joint 900, teeth 912, 914 and pins 922, 924, 926 may extend along a radial direction 952 so that teeth 912, 914 and pins 922, 924, 926 engage and intermesh to a large degree when joint 900 is articulated, such as by rotating discs 910, 920 relative to one another. As a result, as shown in FIG. 11A, pin 924 extends into a recess 944 located between teeth 912, 914 so that teeth 912, 914 and pins 922, 924, 926 may engage and intermesh with one another to a large degree. To facilitate a large range of motion (rotation) between discs 910, 920 in such an embodiment with a high degree of engagement and intermeshing between teeth 912, 914 and pins 922, 924, 926, cutouts 942 may be provided in the sides of a stem 943 to which pin 924 is connected, as shown in FIG. 11A. As a result, when discs 910, 920 are rotated relative to one another along directions 940 and pin 924 and one of teeth 912 or 914 move towards one another, one of the respective sides 913, 915 of teeth 912, 914 may be received within a cutout 942 of pin 924 to provide a high range of motion for joint 900. Further, cutouts 950 may be located laterally to teeth 912, 914, such as adjacent to the base of teeth 912, 914, to accommodate pins 922, 926 at high ranges of motion when discs 910, 920 are rotated relative to one another. A shoulder 951 of disc 910 may engage with a portion of disc 920, such as part of pin 922 or 926, and act as a mechanical stop, as will be discussed below.

Figure 11B:
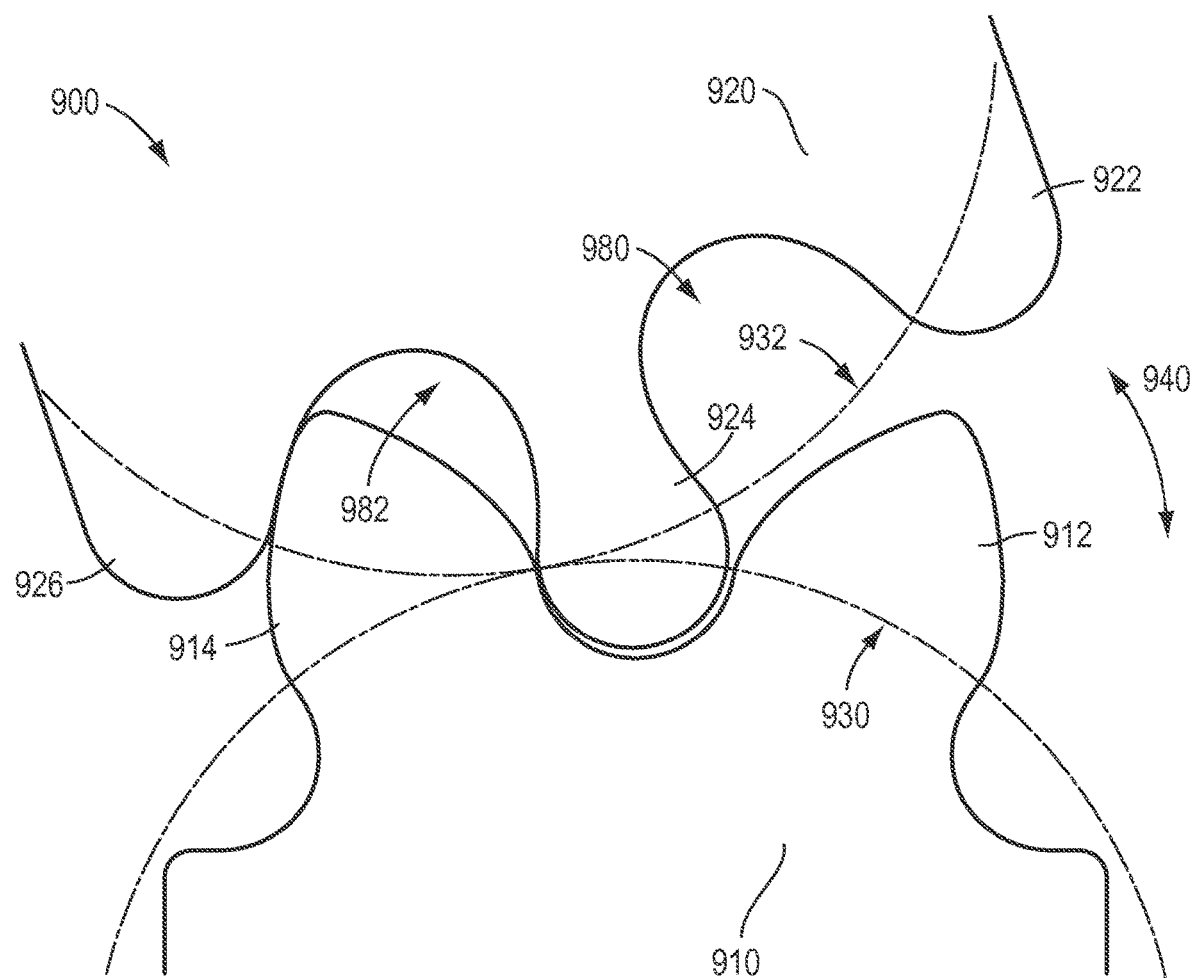
FIG. 11B is a side view of the joint of FIG. 11A during motion of the joint in the counterclockwise direction 940 from the position of FIG. 11A.

As discussed above with regard to the exemplary embodiment of FIGS. 3 and 4, actuation of joint 900 can result in a tooth disengaging from corresponding pins so as to be removed from the tooth recess between the corresponding pins. FIG. 11B depicts joint 900 during motion of joint 900, such as via rotation of disc 910, 920 relative to one another along the counterclockwise direction of arrows 940. While the range of motion depicted in FIGS. 11B-11E is counterclockwise, those having ordinary skill in the art will appreciate that the motions described would also apply to movement in the clockwise direction of 940. Thus, in the symmetrical profiles illustrated in FIG. 11A and various other embodiments depicted, the range of motion includes a +/− (clockwise/counterclockwise) range with respect to the longitudinal axis of the wrist structure. However, wrist joints may also be configured to move in only one direction relative to the longitudinal axis and thus only half of the joint structures (for example, either to the left or the right side of the axis 901 depicted in FIG. 11A) could be provided.

Figure 11C:
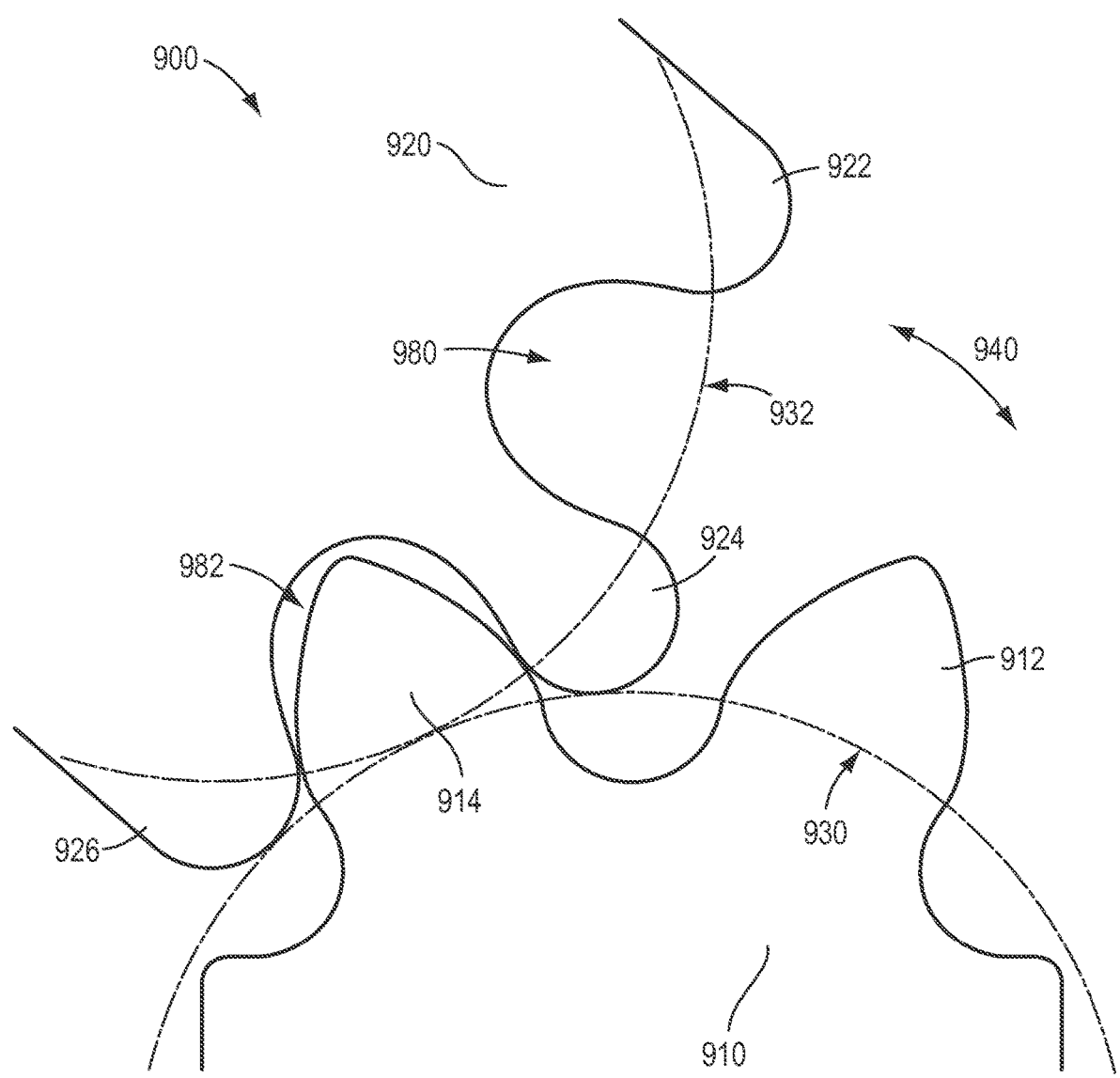
FIG. 11C is a side view of the joint of FIG. 11A as it continues motion in the counterclockwise direction 940 past the position in FIG. 11B.
Figure 11D:
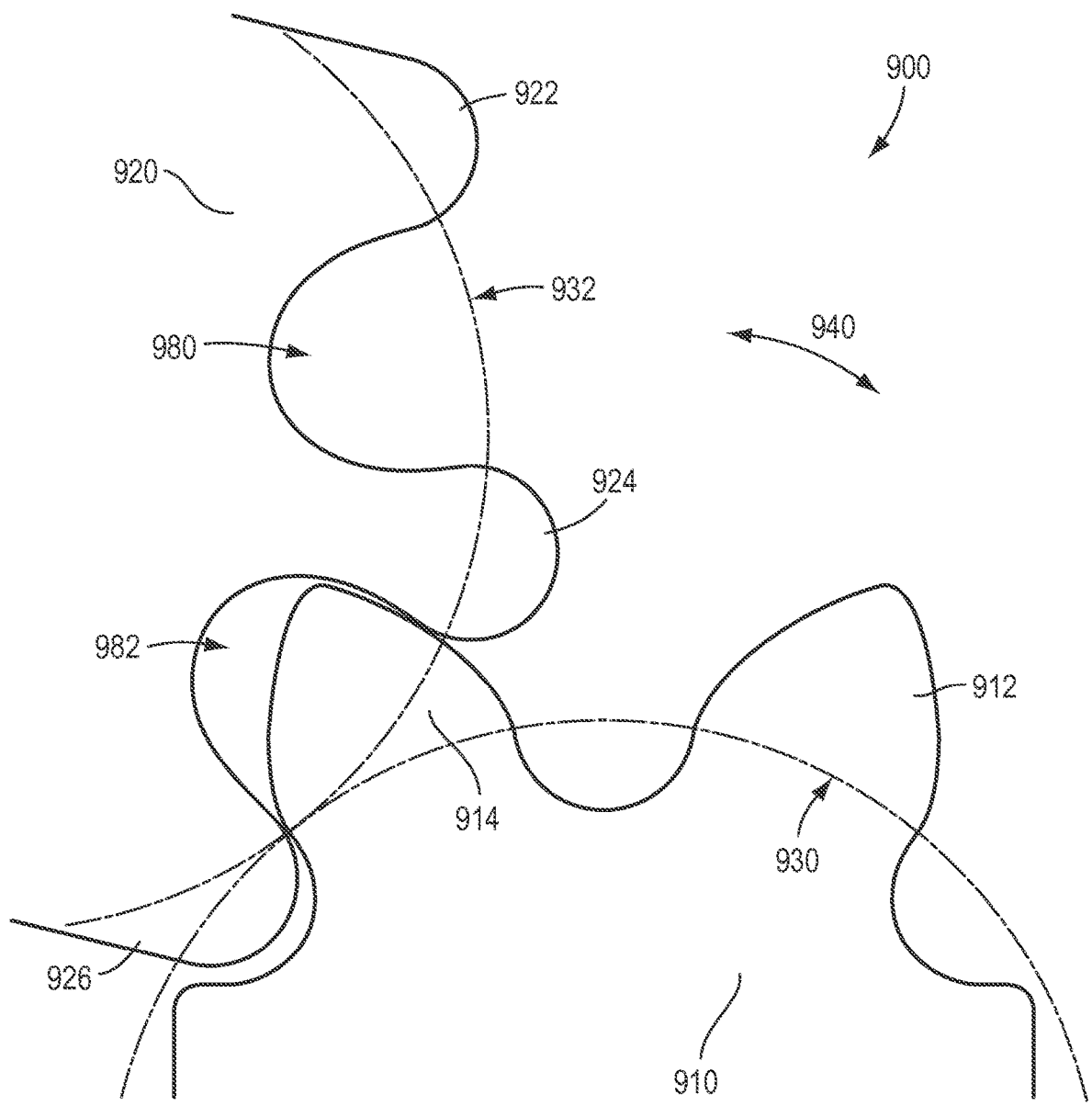
FIG. 11D is a side view of the joint of FIG. 11A as it continues motion in the counterclockwise direction 940 past the position in FIG. 11C.
Figure 11E:
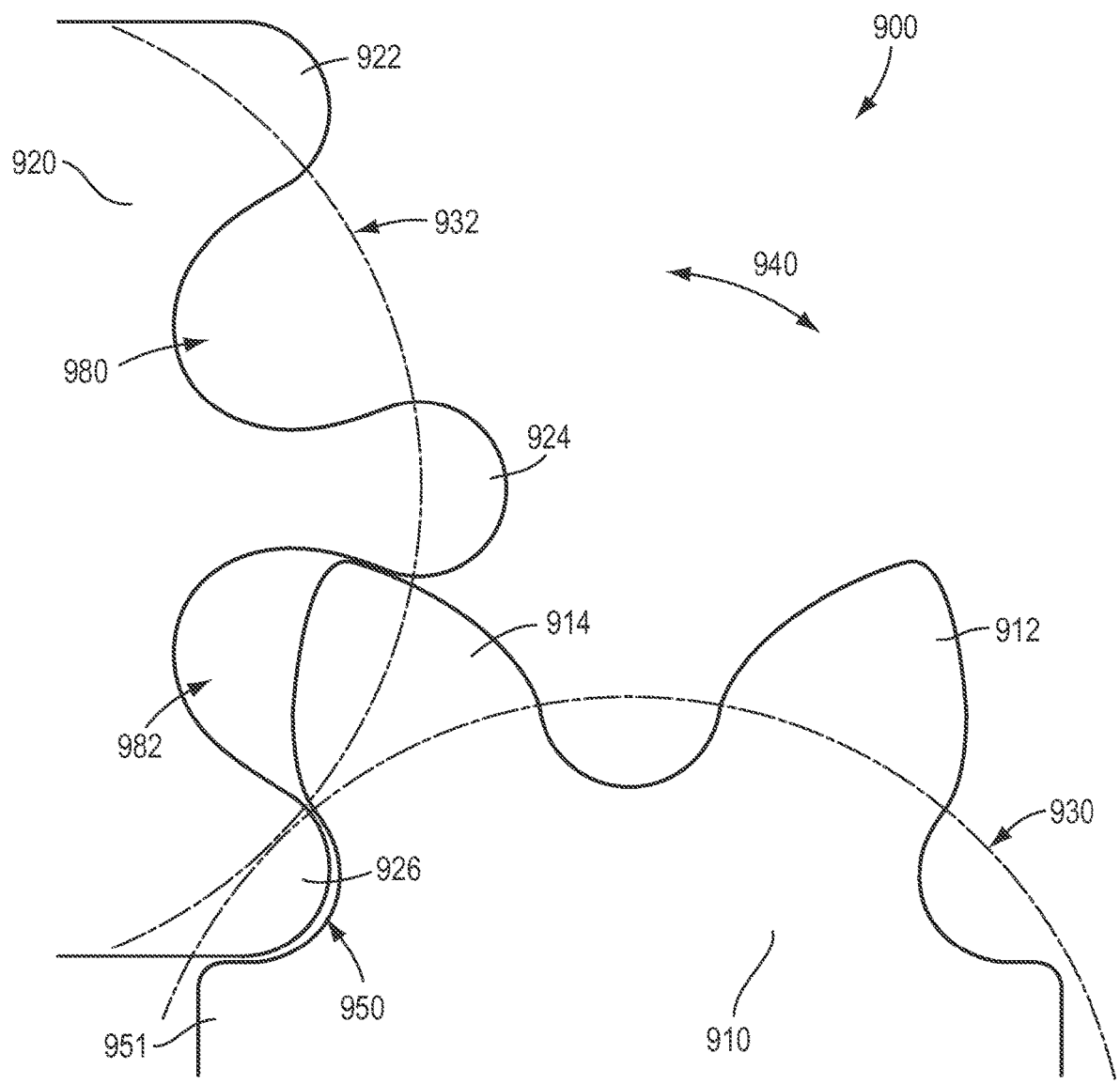
FIG. 11E is a side view of the joint of FIG. 11A in an extreme counterclockwise rotated position.

As shown in FIG. 11B, actuation of joint 900 to roll as depicted causes tooth 914 to extend further into recess 982 of disc 920 between pins 926 and 924 as discs 910, 920. Conversely, tooth 912 begins to withdraw from recess 980 and disengage from pins 922 and 924. The disengagement of tooth 912 from recess 980 between pins 922 and 924 progresses as joint 900 continues to rotate, as shown in FIGS. 11C and 11D, which show tooth 912 completely removed, or disengaged, from recess 980 and from pins 922 and 924. As shown in FIG. 11E, articulation of joint 900 stops once joint 900 has reached its full range of motion (roll limit angle), at which point tooth 912 is completely removed from recess between pins 922 and 924, at least a portion (the majority of in the embodiment of FIG. 11) of tooth 914 remains within recess 982 between pins 926 and 924, and pin 926 engages shoulder 951 of disc 910, which acts as a mechanical stop to assist with stopping articulation and supporting the position of the joint 900 in its extreme range of motion position.

As discussed above with regard to FIG. 11A, discs 910, 920 may include cutouts 942, 950 to facilitate a large range of motion (rotation) between discs 910, 920. Cutouts 942, 950, however, may be difficult to manufacture, in particular, if disc 920 is manufactured by a molding process, because it is difficult to form the cutouts 942, 950 with mold surfaces and then subsequently withdraw the mold surfaces from cutouts 942, 950 due to the shape of cutouts 942, 950 relative to adjacent components of discs 910, 920, particularly when teeth 912, 914 and pins 922, 924, 926 are located radially inward of bearing projections, such as in the exemplary embodiment of FIG. 5. In addition, when teeth 912, 914 and pins 922, 924, 926 are located at a radially inward location, such as in the exemplary embodiment of FIG. 9, the inward location makes machining of teeth 912, 914 and pins 922, 924, 926 challenging.

Figure 12:
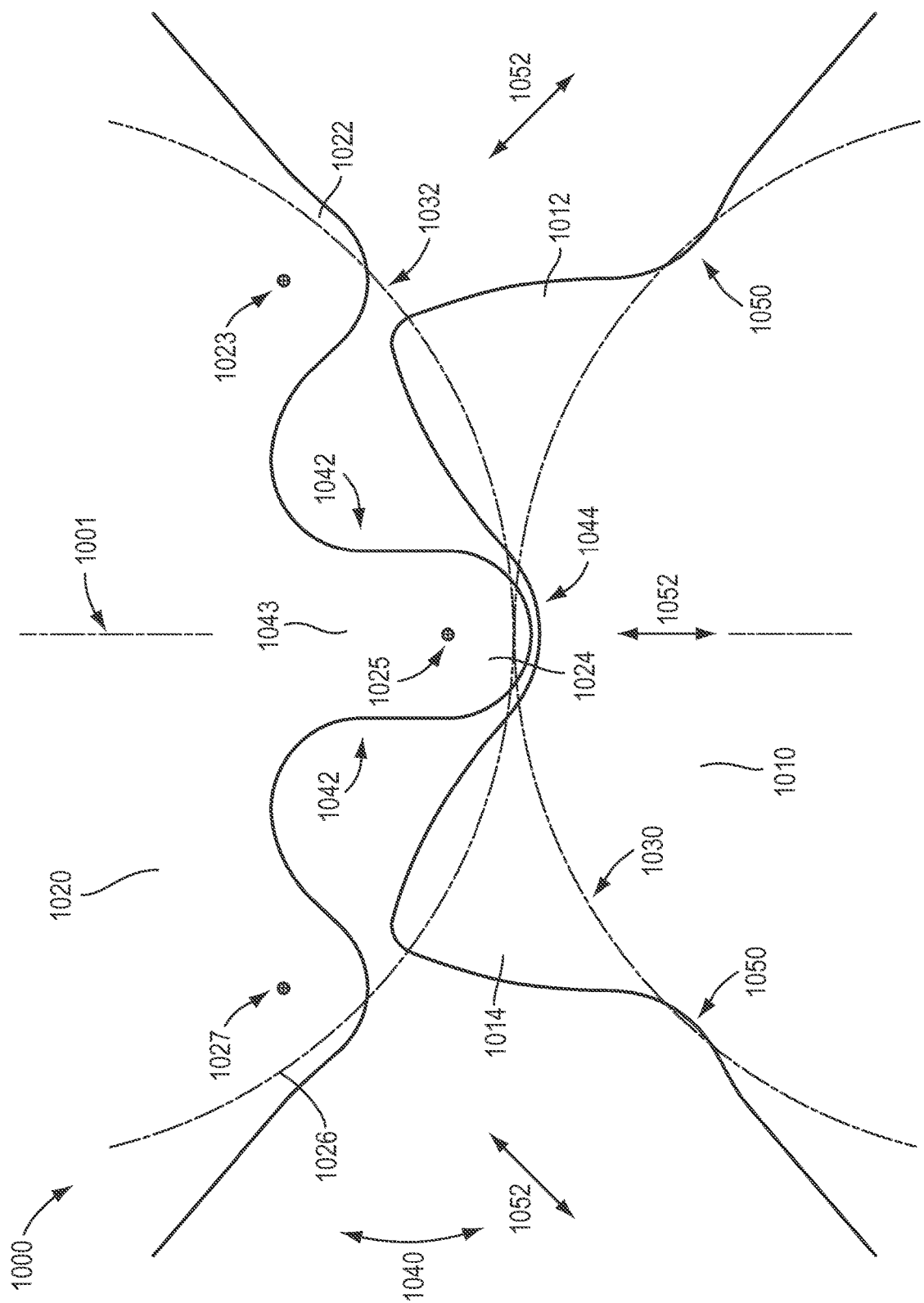
FIG. 12 is a side view of an exemplary embodiment of a joint that includes pins offset from a circular arc projected onto a plane of the pins.

To enhance the ease of manufacturing joint discs, joint discs may be designed with a shape having fewer cutouts or even no cutouts. Turning to FIG. 12, a side view of a joint 1000 is shown that includes a first disc 1010 with teeth 1012, 1014 and a second disc 920 with pins 1022, 1024, 1026, according to an exemplary embodiment. Circular arcs (represented by dashed lines) 1030, 1032 represent contact surfaces between discs 1010, 1020. For instance, circular arcs 1030, 1032 may be projections of surfaces of bearing projections 540, 544, 740, 744 discussed above with regard to the exemplary embodiments of FIGS. 5 and 9, similar to circular arcs 930, 932. Thus, discs 1010, 1020 may rotate relative to one another in directions 1040 as though discs 1010, 1020 act as two circles (represented by circular arcs 1030, 1032) rolling against one another.

In the exemplary embodiment of FIG. 12, teeth 1012, 1014 and pins 1022, 1024, 1026 are shaped to extend along radial direction 1052 to a lesser extent than in the exemplary embodiment of FIG. 11A. As a result, pin centers 1023, 1025, 1027 are offset from circular arc 1032. For instance, in the neutral position shown in FIG. 12, joint 1000 is straight so that a longitudinal axis 1001 passes through centers of both of discs 1010, 1020. Pin centers 1023, 1025, 1027, for example, may be offset from circular arc 1032 by extending toward disc 1010 along radial direction 1052 (which may be a radial direction toward a center of circular arc 1032) a lesser amount than the bearing projection represented by circular arc 1032. Centers 1023, 1025, 1027 of pins 1022, 1024, 1026 may remain on arc 1032 when joint 1000 is articulated. Thus, when discs 1010, 1020 are rotated relative to one another in direction 1040, centers 1023, 1025, 1027 of pins 1022, 1024, 1026 may remain on circular arc 1032 because the distance between pin centers 1023, 1025, 1027 and circular arc 1032 does not substantially change. Because teeth 1012, 1014 and pins 1022, 1024, 1026 extend to a lesser degree along radial direction 1052, sides 1042 of stem 1043 may be substantially straight with no undercuts. In addition, locations 1050 lateral to teeth 1012, 1014 may also lack cutouts, such as cutouts 950 in the exemplary embodiment of FIG. 11A. Thus, discs 1010, 1020 may be easier to manufacture due to fewer cutouts or a lack of undercuts, thereby minimizing or eliminating surface contours that prevent a mold surface from being withdrawn, such as due to interlocking surfaces.

However, because teeth 1012, 1014 and pins 1022, 1024, 1026 extend to a lesser extent along radial direction 1052, teeth 1012, 1014 and pins 1022, 1024, 1026 engage and intermesh to a lesser extent, such as in comparison to the exemplary embodiment of FIG. 11A. As a result, articulation of joint 1000 may be less smooth, such as when discs 1010, 1020 are rotated relative to one another in direction 1040. Further, the degree of timing provided by teeth 1012, 1014 and pins 1022, 1024, 1026 may be diminished in comparison to a joint having greater engagement between teeth and pins, such as in the exemplary embodiment of FIG. 11A.

Figure 13:
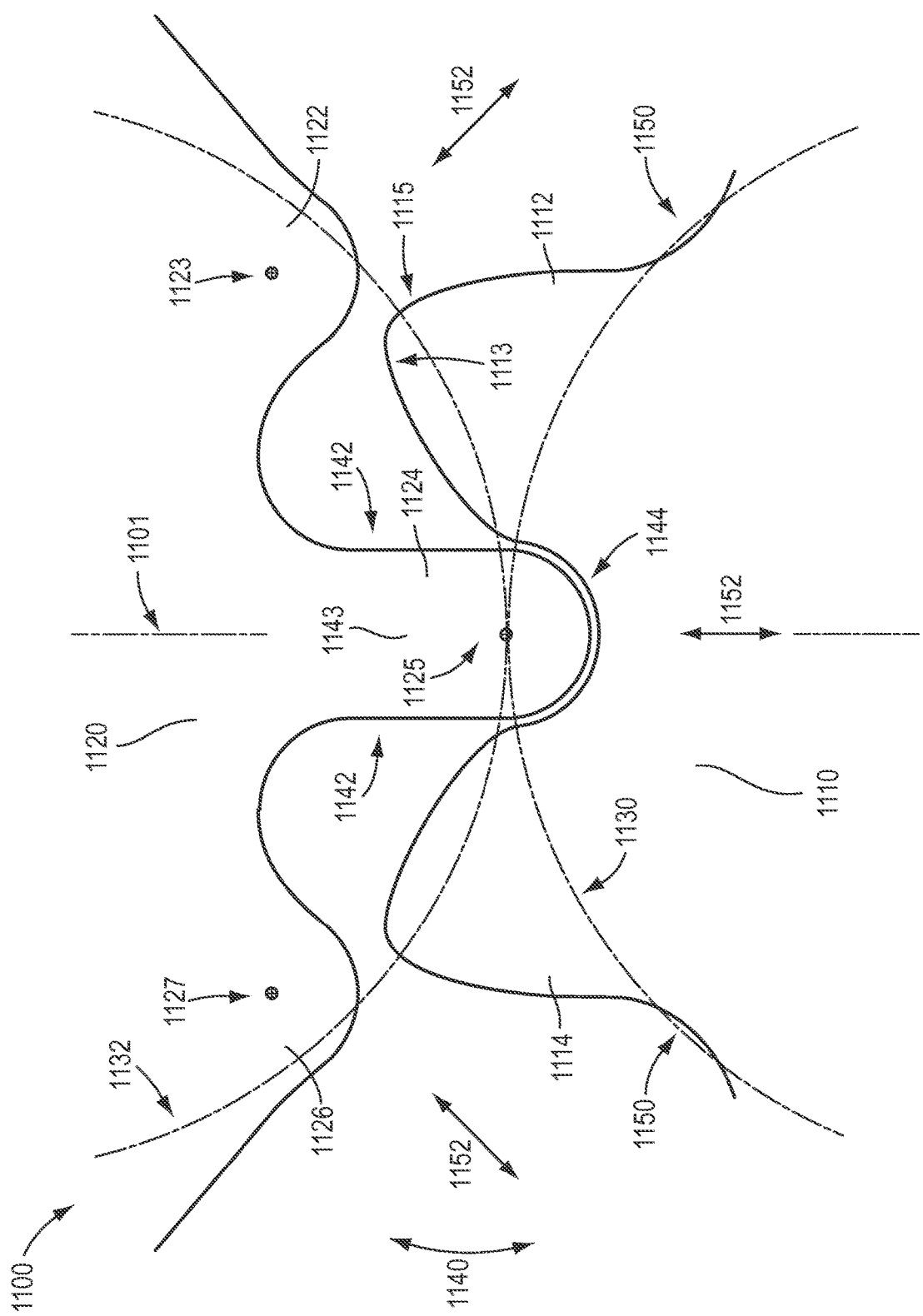
FIG. 13 is a side view of an exemplary embodiment of a joint that includes at least one pin offset from a circular arc projected onto a plane of the pins and at least one pin located on the circular arc.

In view of these considerations, it may be desirable to provide a joint that provides a balance between ease of manufacturing a joint and engagement between teeth and pins of the joint. Turning to FIG. 13, a side view is shown of an exemplary embodiment of a joint 1100 that includes a first disc 1110 having teeth 1112, 1114 and a second disc 1120 having pins 1122, 1124, 1126. Circular arcs (represented by dashed lines) 1130, 1132 represent contact surfaces between discs 1110, 1120. For instance, circular arcs 1130, 1132 may be projections of surfaces of bearing projections 540, 544, 740, 744 discussed above with regard to the exemplary embodiments of FIGS. 5 and 9, similar to circular arcs 930, 932. Thus, discs 1110, 1120 may rotate relative to one another in directions 1140 as though discs 1110, 1120 act as two circles (represented by circular arcs 1130, 1132) rolling against one another.

In the exemplary embodiment of FIG. 13, pins 1122, 1126 are configured to extend along radial direction 1152 to a lesser extent so that pins 1122, 1126 are offset from circular arc 1132, but pin 1124 extends a larger amount along radial direction 1152 than pins 1122, 1126. Because of this, the respective centers 1123, 1127 of pins 1122, 1126 are offset radially from circular arc 1132 along radial direction 1152 but the center 1125 of pin 1124 is located on circular arc 1132. In the neutral position shown in FIG. 13, joint 1100 is straight, for example, so that a longitudinal axis 1101 passes through centers of both of discs 1110, 1120. Further, when discs 1110, 1120 are rotated relative to one another in direction 1140, center 1125 of pin 1124 may remain on circular arc 1132 because the distance between pin centers 1123, 1125, 1127 and circular arc 1132 does not substantially change. In addition, pin 1124 may extend to be received in recess 1144 located between teeth 1112, 1114. As a result, teeth 1112, 1114 and pins 1122, 1124, 1126 engage and intermesh with one another to a greater extent than in the exemplary embodiment of FIG. 12, which may provide smoother motion and enhanced timing in comparison to the exemplary embodiment of FIG. 12. In addition, sides 1142 of stem 1143 from which pin 1124 extends may lack undercuts and locations 1150 lateral to teeth 1112, 1114 may also lack undercuts, facilitating the manufacture of discs 1110, 1120. Thus, by providing a disc 1120 including at least one pin that is axially offset from a circular arc 1132 representing the contact surface between the disc 1120 and a companion disc 1110 of a joint 1100 and at least one pin that is not offset from the circular arc 1132, a balance may be provided between ease of manufacture and engagement between teeth and pins, which affects smoothness of joint motion and joint "timing." Although pin 1124 is not offset from circular arc 1132 and pins 1122, 1126 are offset from circular arc 1132 in the exemplary embodiment of FIG. 13, other configurations may be used. For instance, a disc including four pins may have the two end pins offset from the circular arc representing a contact surface of the disc, while the two middle pins are not offset from the circular arc.

As described, for example with respect to the motions of the joint of FIGS. 11A-11E, it should be appreciated that teeth 1000 and 1100 of the exemplary embodiments of FIGS. 12 and 13 also become removed/withdrawn from with their respective recesses depending on the direction of rotation of the discs during articulation of joints 1000, 1100. Further, the teeth of joints 1000 and 1100 may become disengaged from corresponding pins during articulation of joints 1000, 1100, as discussed above with regard to FIGS. 11B-11E. The sequence of FIGS. 11A to 11E illustrates roll motion between two discs that include contact bearing surfaces and timing structures adjacent the contact bearing surfaces, as the discs roll from an aligned (zero angle) orientation to an example roll limit angle of about 90 degrees. As the two bearing surfaces roll against each other, the outer surfaces of the teeth and corresponding recesses slide past one another until the side of pin 926 jams against shoulder 951 and the outer surface of tooth 914 jams against the outer surface of pin 924 to act as roll angle limit stops. Either one of these jamming roll limit stops may be eliminated in some implementations, or both may be eliminated in other implementations in which a separate mechanical roll limit angle stop is used. In yet other implementations, a mechanical roll limit stop is not used, and the angular relationship between the two discs is controlled so that the angle does not exceed a defined angle that might cause the joint to disengage under anticipated loads.

Joints 900, 1000, 1100 of the exemplary embodiments of FIGS. 11A-13 may also include bearing projections (not shown), as described above in the exemplary embodiments of FIGS. 5 and 9, to bear compressive loads. As noted above, the bearing projections may provide surfaces represented by circular arcs 930, 932, 1030, 1032, 1130, 1132. Such bearing projections may permit teeth and pins of joints 900, 1000, 1100 to remain spaced apart from one another. For instance, bearing projections included in joint 1000 of the exemplary embodiment of FIG. 12 may permit teeth 1012, 1014 and pins 1022, 1024, 1026 to be spaced from one another during normal circumstances (e.g., when a lateral force and/or torque is not applied to joint 1000), as indicated in the exemplary embodiment of FIG. 12. Alternatively, the joints of the exemplary embodiments of FIGS. 11A-13 may lack bearing projections, with teeth and pins of the joints bearing compressive loads. In particular, joints 900 and 1100 of FIGS. 15 and 17 could lack projections, with teeth 912, 914 and pins 922, 924, 926 of joint 900 bearing compressive loads and recess 1144 and teeth 1112, 1114 bearing compressive load with pin 1124 of joint 1100 when discs 1110, 1120 are in the positions shown in the exemplary embodiment of FIG. 13.

Figure 14:
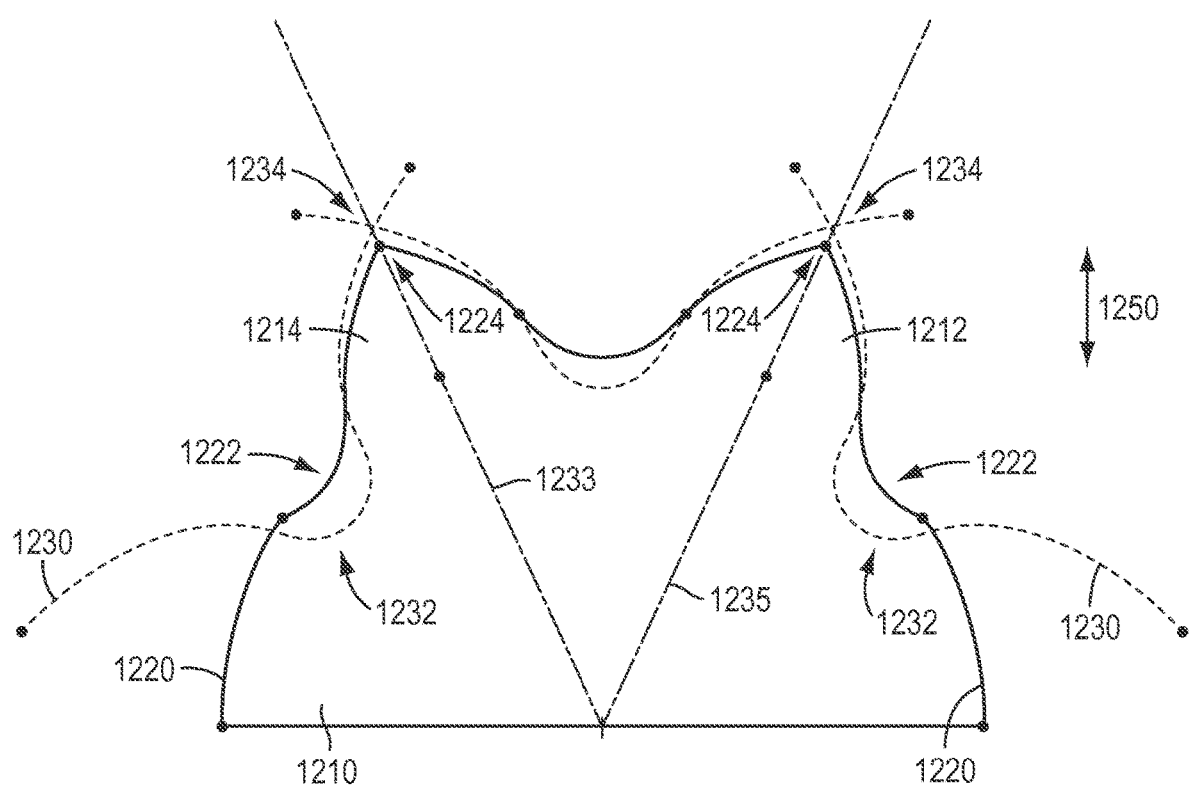
FIG. 14 is a side view of an exemplary embodiment of a disc showing a comparison between discs having pins not offset from a circular arc and pins offset from a circular arc.

By utilizing a configuration in which one or more pins are offset from a circular arc, a shape of the pins and teeth may be altered. For instance, teeth 1112, 1114 may be more asymmetrically shaped than teeth 912, 914 in the exemplary embodiment of FIG. 11A (in which pin centers 923, 925, 927 lie on circular arc 932), with a first side 1113 of tooth 1112 following a curvature different than second side 1115 of tooth 1112. Asymmetrically shaped teeth can affect the engagement between teeth and pins, as well as the reduction or elimination of cutouts. Turning to FIG. 14, an exemplary embodiment of a disc 1210 is shown, with line 1220 outlining a shape of teeth 1212, 1214 when corresponding pins (not shown) are offset from a circular arc, such as in the exemplary embodiment of FIG. 12. In contrast, line 1230 represents the shape of teeth 1212, 1214 when corresponding pins (not shown) are not offset from a circular arc, such as in the exemplary embodiment of FIG. 11A. When some pins are offset and some are not, such as in the exemplary embodiment of FIG. 13, teeth 1212, 1214 may have a shape that is a hybrid of lines 1220, 1230. Lines 1233, 1235 may be longitudinal axes of teeth 1212, 1214 and may extend through tips 1234 of teeth 1212, 1214, as shown in FIG. 14. A comparison between lines 1220, 1230 shows line 1232 provides a more symmetrical shape for teeth 1212, 1214 than line 1220. Further, line 1220 reduces or eliminates cutouts 1232 (indicated by line 1230), which would otherwise be located at lateral locations 1222. In addition, line 1220 may result in a reduction of the amount that tooth tips 1224 extend along direction 1250, in comparison to the tooth tips 1234 provided by line 1230.

The exemplary embodiments and methods described herein have been described as being utilized with surgical and other instruments for teleoperated surgical systems. However, the exemplary embodiments and methods described herein may be used with other types of devices, such as laparoscopic instruments and other hand held instruments that use jointed motion.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical instrument comprising:
   a wrist comprising:
   a first disc comprising a first pair of joint features and a first pair of load bearing surfaces, the first pair of joint features positioned diametrically opposite one another, the first pair of load bearing surfaces positioned diametrically opposite one another, and the first pair of load bearing surfaces radially offset from the first pair of joint features;
   a second disc adjacent the first disc, the second disc comprising a second pair of joint features and a second pair of load bearing surfaces, the second pair of joint features positioned diametrically opposite one another, the second pair of load bearing surfaces positioned diametrically opposite one another, and the second pair of load bearing surfaces radially offset from the second pair of joint features; and
   a drive tendon extending through the first disc and the second disc;
   wherein the first pair of joint features and the second pair of joint features oppose and intermesh with each other;
   wherein each joint feature of the first pair of joint features comprises one of a plurality of teeth and a plurality of pins, and each joint feature of the second pair of joint features comprises the other of the plurality of teeth and the plurality of pins, each tooth of the plurality of teeth having a first surface profile, and each pin of the plurality of pins having a second surface profile differing from the first surface profile;
   wherein one or both of the first surface profile and the second surface profile comprises a cycloidal surface profile; and
   wherein the drive tendon is configured to exert a force on at least one of the first and second discs to cause relative rotation between the first and second discs.

2. The surgical instrument of claim 1, wherein the first and second pairs of load bearing surfaces are located radially inward, relative to a longitudinal axis of the wrist, of the first and second pairs of joint features of each of the first and second discs.

3. The surgical instrument of claim 1, wherein the first and second pairs of load bearing surfaces are located radially outward, relative to a longitudinal axis of the wrist, of the first and second pairs of joint features of each of the first and second discs.

4. The surgical instrument of claim 1, wherein the first surface profile and the second surface profile each comprise the cycloidal surface profile.

5. The surgical instrument of claim 1, wherein the other of the first and second pair of joint features comprising the plurality of pins includes at least one recess having a trochoid shape and configured to receive one of the plurality of teeth.

6. The surgical instrument of claim 1, wherein centers of each of the plurality of pins are located on a circular arc, wherein the circular arc is a projection of the respective one of the first and second pairs of load bearing surfaces of the one of the first disc and the second disc associated with the one of the first and second pair of joint features comprising the plurality of pins, and wherein the projection is onto a plane of the plurality of pins.

7. The surgical instrument of claim 1, wherein centers of each of the plurality of pins are radially offset from a circular arc, wherein the circular arc is a projection of the respective one of the first and second pairs of load bearing surfaces of the one of the first disc and the second disc associated with the one of the first and second pair of joint features comprising the plurality of pins, and wherein the projection is onto a plane of the plurality of pins.

8. The surgical instrument of claim 1, wherein at least one center of the pins is offset from a circular arc, wherein the circular arc is a projection of the respective one of the first and second pairs of load bearing surfaces of the one of the first disc and the second disc associated with the one of the first and second pair of joint features comprising the plurality of pins, wherein a center of at least one of the pins is located on the circular arc, and wherein the projection is onto a plane of the plurality of pins.

9. The surgical instrument of claim 1, wherein centers of at least two pins of the plurality of pins are radially offset different distances from a circular arc, wherein the circular arc is a projection of the respective one of the first and second pairs of load bearing surfaces of the one of the first disc and the second disc associated with the one of the first and second pair of joint features comprising the plurality of pins, and wherein the projection is onto a plane of the plurality of pins.

10. The surgical instrument of claim 1, wherein at least one pin of the plurality of pins has a constant radius of curvature.

11. The surgical instrument of claim 1, wherein at least two pins of the plurality of pins differ in diameter.

12. The surgical instrument of claim 1, wherein at least one of the teeth of the plurality of teeth is a separate piece from the one of the first and second disc.

13. The surgical instrument of claim 1, wherein at least one pin of the plurality of pins is a separate piece from the other of the first and second disc.

14. The surgical instrument of claim 1, wherein the each of the first and second pair of load bearing surfaces has a partial-cylinder shape.

15. The surgical instrument of claim 1, wherein each of the first and second pair of load bearing surfaces has a cycloidal shape.

16. The surgical instrument of claim 1, wherein the wrist has a diameter of about 3 mm to about 13 mm.

17. The surgical instrument of claim 1, wherein the relative rotation between the first and second discs has a maximum rotational range of motion greater than about ±45 degrees.

18. The surgical instrument of claim 17, wherein the relative rotation between the first and second discs is from 0 degrees through ±75 degrees.

19. The surgical instrument of claim 17, wherein the relative rotation between the first and second discs is from 0 degrees through ±90 degrees.

* * * * *